US008852589B2

(12) United States Patent
McKenzie et al.

(10) Patent No.: US 8,852,589 B2
(45) Date of Patent: Oct. 7, 2014

(54) ANTIBODIES AGAINST IL-17BR

(71) Applicant: Medical Research Council, London (GB)

(72) Inventors: Andrew Neil James McKenzie, Cambridge (GB); Daniel Neill, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 14/056,559

(22) Filed: Oct. 17, 2013

(65) Prior Publication Data

US 2014/0044718 A1    Feb. 13, 2014

Related U.S. Application Data

(62) Division of application No. 13/262,123, filed as application No. PCT/GB2010/000639 on Mar. 31, 2010, now Pat. No. 8,586,037.

(60) Provisional application No. 61/166,808, filed on Apr. 6, 2009.

(30) Foreign Application Priority Data

Apr. 6, 2009 (GB) .................................. 0905972.6

(51) Int. Cl.
*A61K 39/00* (2006.01)
*A61K 39/395* (2006.01)
*C07K 16/24* (2006.01)
*C07K 16/28* (2006.01)

(52) U.S. Cl.
CPC .......... *C07K 16/244* (2013.01); *C07K 2317/33* (2013.01); *C07K 2317/76* (2013.01); *A61K 2039/505* (2013.01); *C07K 16/2866* (2013.01)
USPC .................. 424/130.1; 424/133.3; 424/135.1; 424/139.1; 424/141.1; 424/142.1; 424/143.1

(58) Field of Classification Search
None
See application file for complete search history.

(56) References Cited

U.S. PATENT DOCUMENTS

2011/0052600 A1* 3/2011 Budelsky et al. .......... 424/158.1

FOREIGN PATENT DOCUMENTS

| WO | WO-00/55204 A1 | 9/2000 |
| WO | WO-01/46420 A2 | 6/2001 |
| WO | WO-01/57202 A2 | 8/2001 |
| WO | WO-01/68705 A2 | 9/2001 |
| WO | WO-2008/129263 A1 | 10/2008 |
| WO | WO-2008/131376 A2 | 10/2008 |
| WO | WO-2009/069355 A1 | 6/2009 |
| WO | WO-2009/136976 A2 | 11/2009 |

OTHER PUBLICATIONS

Morrison et al. (2009, Aust. Fam. Physician 38:956-961).*
Mayer (2010, Gastroenterol. 45:9-16).*
Angkasekwinai et al., "The role of IL-25 in airway allergic response," J Allergy Clin Immunol. 119:S134 (Abstract only) (2007).
Ballantyne et al., "Blocking IL-25 prevents airway hyperresponsiveness in allergic asthma," J Allergy Clin Immunol. 120(6):1324-31 (2007).
Casset et al., "A peptide mimetic of an anti-CD4 monoclonal antibody by rational design," Biochem Biophys Res Commun. 307(1):198-205 (2003).
Chen et al., "Selection and analysis of an optimized anti-VEGF antibody: crystal structure of an affinity-matured Fab in complex with antigen," J Mol Biol. 293(4):865-81 (1999).
Davies et al., "Affinity improvement of single antibody VH domains: residues in all three hypervariable regions affect antigen binding," Immunotechnology. 2(3):169-79 (1996).
Gelfand, "Advances in therapy for adult asthma," Clinical Cornerstone. 8(4):62-75 (2007).
Holm et al., "Functional mapping and single chain construction of the anti-cytokeratin 8 monoclonal antibody TS1," Mol Immunol. 44(6):1075-84 (2007).
Holt et al., "Domain antibodies: proteins for therapy," Trends Biotechnol. 21(11):484-90 (2003).
Lajoie-Kadoch et al., "TNF-alpha and IFN-gamma inversely modulate expression of the IL-17E receptor in airway smooth muscle cells," Am J Physiol Lung Cell Mol Physiol. 290(6):1238-1246 (2006).
Letuve et al., "IL-17E upregulates the expression of proinflammatory cytokines in lung fibroblasts," J Allergy Clin Immunol. 117(3): 590-6 (2006).
MacCallum et al., "Antibody-antigen interactions: contact analysis and binding site topography," J Mol Biol. 262(5):732-45 (1996).
Neill et al., "Nuocytes represent a new innate effector leukocyte that mediates type-2 immunity," Nature. 464(7293):1367-70 (2010).
Paul, Strucutre and function of immunoglobulins. *Fundamental Immunology*. William E. Paul, 292-295 (1993).
Rickel et al, "Identification of functional roles for both IL-17RB and IL-17RA in mediating IL-25-induced activities," J Immunol. 181(6):4299-4310 (2008).
Terashima et al., "A novel subset of mouse NKT cells bearing the IL-17 receptor B responds to IL-25 and contributes to airway hyperactivity," J Exper Med. 205(12):2727-33 (2008).
Terashima et al., "A novel subset of mouse NKT cells bearing the IL-17 receptor B responds to IL-25 and contributes to airway hyperreactivity," J Exp Med. 205(12):supplemental pp. 1-3 (2008).
Vajdos et al., "Comprehensive functional maps of the antigen-binding site of an anti-ErbB2 antibody obtained with shotgun scanning mutagenesis," J Mol Biol. 320(2):415-28 (2002).
Wang et al., "IL-25 augments type 2 immune responses by enhancing the expansion and functions of TSLP-DC-activated Th2 memory cells," J Exp Med. 204(8):1837-47 (2007).
Search Report for United Kingdom Patent Application No. GB0905972.6, dated Aug. 6, 2009 (8 pages).
International Search Report and Written Opinion of the International Searching Authority for International Application No. PCT/GB2010/000639, mailed Jul. 28, 2010 (15 pages).

* cited by examiner

*Primary Examiner* — Elizabeth C Kemmerer
(74) *Attorney, Agent, or Firm* — Clark & Elbing LLP

(57) ABSTRACT

The invention provides the antibody D9.2 and antibody molecules based on D9.2 which bind interleukin-17 receptor B. These may be useful in therapy, e.g. the treatment of asthma, ulcerative colitis or Crohn's disease.

10 Claims, 9 Drawing Sheets

ANTIBODIES AGAINST IL-17BR

FIELD OF THE INVENTION

The present invention relates to antibodies, including binding fragments thereof, directed to interleukin 17B receptor (IL-17BR).

BACKGROUND TO THE INVENTION

Asthma is a common chronic inflammatory disorder of the airways. The number of sufferers has increased dramatically over recent decades and the World Health Organisation estimates that in the region of 300 million people worldwide suffer from asthma. Allergic asthma is characterised by uncontrollable airways hyperresponsiveness (AHR) induced by a variety of provocative stimuli and is associated with type-2 inflammatory infiltrates into the lungs.

Inflammatory bowel disease (IBD) is a chronic inflammation affecting the mucosal layer of the colon (also known as the large intestine), which includes two disease conditions: ulcerative colitis (UC) and Crohn's disease (CD). Conventional therapies for treatment of IBD involve either antibiotics or steroid-derived drugs or anti-TNF-α agents; however, these are not currently successful in inducing or maintaining clinical remission in patients (Hanauer et al., 2008). UC is thought to be a Th2-mediated disease, with a representative mouse model showing involvement of type 2 cytokines in the development of gut inflammation (Heller et al., 2002)

The interleukin-17B receptor, variously known as IL-25R, IL-17BR, IL-17RB or IL-17RH1 was first identified in an expressed sequence tag database by its homology to the IL-17A receptor (IL-17RA) (Tian et al., 2000). IL-17BR has subsequently been shown to bind both IL-17B and IL-25 (Lee et al., 2001; Shi et al., 2000; Tian et al., 2000). IL-25 binds to IL-17BR with a stronger affinity (1.4 nM) than IL-17B (7.6 nM).

IL-25, a member of the IL-17 cytokine family (IL-17A, IL-17B, IL-17C, IL-17D and IL-17F—associated with type-1 inflammation), differs strikingly from other IL-17 family members in that its production induces type-2 cytokine expression associated with splenomegaly, elevated serum levels of IgG1 and IgE and pathological changes in the lungs and digestive tract including eosinophilic infiltrates, increased mucus secretion and epithelial cell hyperplasia (Fort et al., 2001; Lee et al., 2001; Moseley et al., 2003; Pan et al., 2001). Genetic ablation of IL-25 or the use of blocking anti-IL-25 antibodies have clearly demonstrated the importance of IL-25 in protecting from helminth infection (Fallon et al., 2006; Owyang et al., 2006), but also its critical role in regulating responses characteristic of asthma (Ballantyne et al., 2007). It appears that IL-25 stimulates these responses through its ability to induce the release of type-2 cytokines, such as IL-13, initially from innate non-B/non-T (NBNT) cells (Fallon et al., 2006; Fort et al., 2001) and subsequently from the adaptive T cell response (Angkasekwinai et al., 2007; Wang et al., 2007).

il17br message has been identified in libraries from lung, brain, pancreas, kidney, thyroid and eosinophils (Lee et al., 2001; Shi et al., 2000). Expression in lung smooth muscle cells seems to be immunologically regulated (Lajoie-Kadoch et al., 2006).

Consistent with a role in asthma, IL-25 mRNA or protein has been detected from a number of cell types found in the lung including alveolar macrophages, mast cells, eosinophils, and basophils (Wang et al., 2007). More recently, IL-25 production by allergen-stimulated human and mouse lung epithelial cells has supported a potential role for IL-25 modulating allergic pulmonary responses (Angkasekwinai et al., 2007). In addition, IL-25 has been reported to induce inflammatory cytokine and chemokine production from lung fibroblasts, and components of extra-cellular matrix from airway smooth muscle cells. Furthermore, recent studies have indicated that transcripts for IL-25 and IL-17BR are significantly upregulated in biopsy tissue from asthmatic patients, associated with eosinophilic infiltration (Wang et al., 2007). Treatment of OVA sensitised mice with a blocking monoclonal antibody directed against IL-25 results in a decreased AHR and lower IL-13 concentrations in the bronchoalveolar lavage in response to OVA challenge and methacholine administration.

Recently, Rickel et al. (*J Immunol* 181, 4299-4310 (2008)) used a blocking monoclonal antibody to human IL-17RA to prevent IL-25 activity in a primary human cell-based assay. This showed that IL-25 activity requires both IL-17BR and IL-17RA. However, it has also been reported that IL-17A and IL-17F signal through a heteromeric complex containing IL-17RA and IL-17RC.

Rickel et al. also describe an antibody reactive with mouse IL-17BR which blocks IL-25-induced lung inflammation in a mouse model of allergic asthma. To date, no antibodies reactive with human IL-17BR have been reported.

Consistent with a role in IBD, IL-25 production has been observed in an experimental model of chronic colitis in mouse, in association with a switch from a Th1 to a Th2 type response (Fichtner-Feigl et al., 2008) and high mRNA expression of IL-25 was found throughout the gastrointestinal tract in mice (Fort et al., 2001). Moreover the IL-25 gene is located within a Crohn's disease susceptibility region on chromosome 14 in humans, although its potential association with the disease remains to be investigated (Buning et al., 2003).

DISCLOSURE OF THE INVENTION

The present inventors have identified an antibody molecule which binds with high affinity and specificity to IL-17BR.

Antibody molecules described herein may be useful in blocking IL-25 bioactivity in vivo, and preventing airways inflammation, AHR, and inflammation of the colon.

In antigen challenged mice, administration of an antibody molecule described herein is shown to reduce levels of IL-13 and IL-5, both of which are critical cytokines in asthma regulation, and to reduce numbers of IL-13-producing cells in the lungs to levels and numbers similar to those found in the absence of antigen challenge or in antigen challenged IL-17BR-deficient mice. Antibody molecules described herein may also significantly reduce airways hyperreactivity. Furthermore, antibody molecules described herein may reduce disease-related expansion of gamma/delta T cells in vivo. This provides indication that antibody molecules described herein inhibit two pathways known to be essential in the development of asthma; IL-13 production and gamma/delta T cell responsiveness.

The above described antigen challenged mice were challenged with OVA (ovalbumin) antigen in an experimental model of asthma. In mice challenged with OXA (oxazolone) antigen in an experimental model of IBD, administration of an antibody molecule described herein is shown to reduce the mortality rate and clinical signs of IBD, such as weight loss and the shortening of the colon that results from inflammation and haemorrhage.

Antibody molecules described herein may cross-react with both mouse and human IL-17BR and may inhibit binding of human IL-25 to the human IL-17BR. Thus, the antibody molecules may be used in mouse models to investigate its mechanisms of action in vivo. Furthermore, antibody molecules described herein may block the biological action of the IL-25/IL-17BR complex in human cells. Antibody molecules described herein therefore have potential utility for treatment of disease, such as asthma.

An aspect of the invention provides an antibody molecule which binds IL-17BR and which comprises an antibody VH domain comprising a VH CDR3 with the amino acid sequence of SEQ ID NO: 7.

Preferably, an antibody molecule blocks IL-17BR binding to IL-25 and reduces or inhibits at least one of IL-25-mediated AHR; IL-13 production; IL-25-mediated IL-5 production; IL-25-mediated IL-8 production; and gamma/delta T cell expansion and infiltration.

An antibody molecule may comprise a VH domain which comprises a VH CDR3 of SEQ ID NO: 7 together with a CDR1 of SEQ ID NO: 5 and a CDR2 of SEQ ID NO: 6.

A VH domain may be paired with a VL domain, for example a VL domain with a CDR1 of SEQ ID NO: 8, a CDR2 of SEQ ID NO: 9 and a CDR3 of SEQ ID NO: 10. In some embodiments, a VH domain may be paired with a VL domain of SEQ ID NO: 4.

In some embodiments, an antibody molecule may comprise a VH domain which comprises a VH CDR1 of SEQ ID NO:5, a VH CDR2 of SEQ ID NO:6 and a VH CDR3 of SEQ ID NO:7 and a VL domain which comprises a VL CDR1 of SEQ ID NO:8, a VL CDR2 of SEQ ID NO:9 and a VL CDR3 of SEQ ID NO:10.

A VH domain may further comprise human or non-human framework regions, for example the framework regions shown in SEQ ID NO: 2. In some embodiments, the antibody molecule may comprise the VH domain of SEQ ID NO: 2.

A VL domain may further comprise human or non-human framework regions, for example the framework region shown in SEQ ID NO: 4. In some embodiments, the antibody molecule may comprise the VL domain of SEQ ID NO: 4.

In some embodiments, the antibody molecule may comprise the VH domain of SEQ ID NO: 2 and the VL domain of SEQ ID NO: 4.

Aspects of the invention also provide isolated nucleic acid encoding the antibody molecules described herein, vectors comprising the nucleic acid and methods of expressing the nucleic acid in a host cell to produce antibody molecules of the invention.

The invention further provides the use of antibody molecules of the invention, for example in the form of a pharmaceutical composition, for the treatment of disease, for example IL-25 mediated diseases such as allergy, asthma and colitis.

These and further aspects of the invention are described in further detail below and with reference to the accompanying examples.

SEQUENCES

Figure 1:
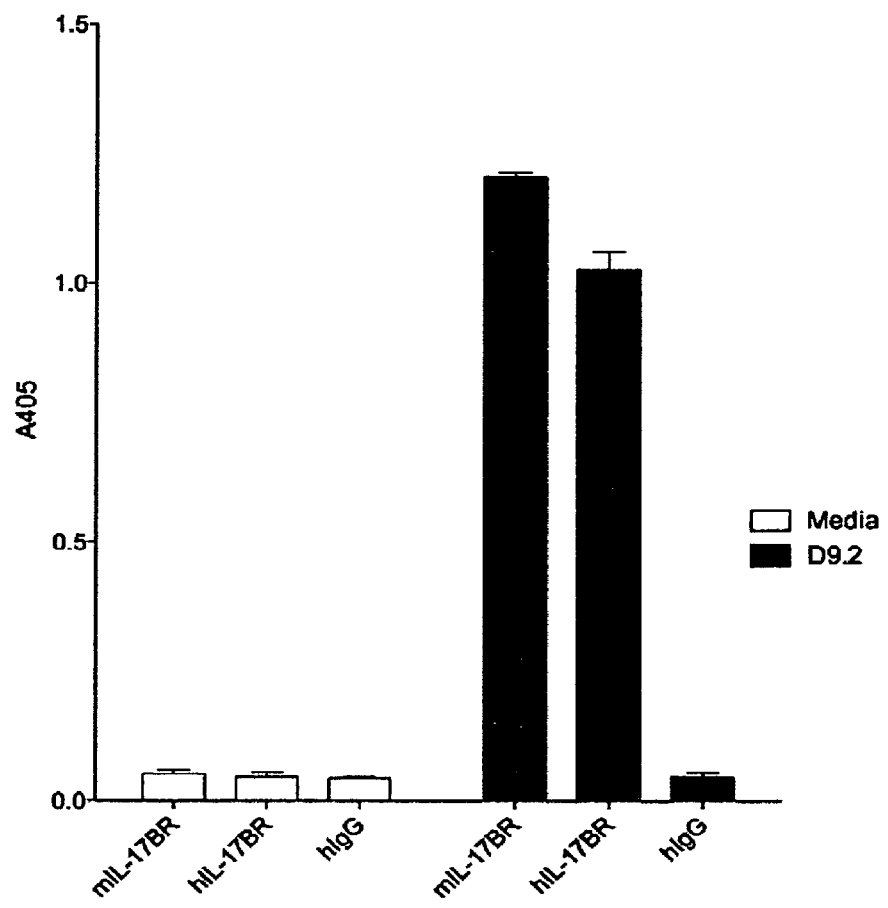
FIG. 1 shows that anti-IL-17BR clone D9.2 is cross-reactive for human and murine IL-17BR binding by ELISA. Bars show binding of media (white bars) or D9.2 antibody clone (black bars) to immobilised murine IL-17BR-Fc, human IL-17BR-Fc or human IgG control.

The antibody molecules of the present invention are described further herein with reference to the following sequence identification numbers:
SEQ ID NO:1 D9.2 VH encoding nucleotide sequence
SEQ ID NO:2 D9.2 VH amino acid sequence
SEQ ID NO:3 D9.2 VL encoding nucleotide sequence
SEQ ID NO:4 D9.2 VL amino acid sequence
SEQ ID NO:5 D9.2 VH CDR1 amino acid sequence
SEQ ID NO:6 D9.2 VH CDR2 amino acid sequence
SEQ ID NO:7 D9.2 VH CDR3 amino acid sequence
SEQ ID NO:8 D9.2 VL CDR1 amino acid sequence
SEQ ID NO:9 D9.2 VL CDR2 amino acid sequence
SEQ ID NO:10 D9.2 VL CDR3 amino acid sequence Further sequences are set out in the accompanying sequence listing.

DETAILED DESCRIPTION OF THE INVENTION

This application is concerned with antigen-antibody type reactions.

In general, the heavy chain variable region (VH domain) of an antibody plays a significant role in the binding of an antibody to an antigen. The CDR3 region of a VH domain has been found to be more diverse than the CDR1 and CDR2 regions, and thus in most antibodies provides specificity for the target of the antibody. Thus antibody molecules of the invention are based around the VH CDR3 region of the D9.2 antibody. In some preferred embodiments, antibody molecules of the invention comprise all three CDRs of the VH regions of the D9.2 antibody.

The structure of an antibody molecule which comprises a CDR of the invention will generally be of a heavy or light chain sequence of an antibody molecule or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human'Services. 1987, and updates thereof. A number of academic and commercial on-line resources are available to query this database. For example, see Martin, A.C.R. Accessing the Kabat Antibody Sequence Database by Computer *PROTEINS: Structure, Function and Genetics,* 25 (1996), 130-133 and the associated on-line resource.

Generally, an antibody molecule comprises a VH domain which is paired with a VL domain to provide an antibody antigen binding domain, although in some embodiments, a VH domain alone may be used to bind antigen. For example, the D9.2 VH domain (SEQ ID NO: 2) may be paired with the D9.2 VL domain (SEQ ID NO: 4), so that an antibody antigen binding site is formed which comprises both the D9.2 VH and VL domains. Alternatively, the D9.2 VH domain may be paired with a VL domain other than the D9.2 VL domain.

Light-chain promiscuity is well established in the art, as discussed further herein.

An antibody molecule described herein may bind human IL-17BR and/or mouse IL-17BR. For example, an antibody molecule may bind human IL-17BR and show no binding or substantially no binding to mouse IL-17BR. Alternatively, an antibody molecule of the invention may bind mouse IL-17BR and show no binding or substantially no binding to human IL-17BR.

Preferably, antibody molecules of the invention are cross reactive with both human and mouse IL-17BR. For example, a cross reactive antibody molecule binds both human IL-17BR and mouse IL-17BR.

An antibody molecule as described herein may bind IL-17BR with an affinity which is substantially similar to that of D9.2, e.g. 90% to 110% of the binding affinity of D9.2. An antibody molecule will generally be specific for IL-17BR. In other words, an antibody molecule may bind IL-17BR but show no binding or substantially no binding to other members of the IL-17R family. Preferably, an antibody molecule specific for IL-17BR binds IL-17BR but shows no binding or substantially no binding to IL-17RA, IL-17RC and/or IL-17RD.

Typically, specificity may be determined by means of a binding assay such as ELISA employing a panel of antigens.

Binding of an antibody molecule described herein with IL-17BR may be abolished by competition with recombinant IL-17BR.

Binding affinity and neutralisation potency of different antibody molecules described herein can be compared under appropriate conditions using routine techniques.

Antibody molecules include any binding member or substance having an antibody antigen-binding site with the required specificity and/or binding to IL-17BR. Examples of antibody molecules include immunoglobulin isotypes and their isotypic subclasses; antibody fragments, such as Fab, Fab', Fab'-SH, scFv, Fv, dAb and Fd; engineered antibody molecules, such as Fab$_2$, Fab$_3$, diabodies, triabodies, tetrabodies and minibodies; and any other polypeptide comprising an antibody antigen-binding site, whether natural or wholly or partially synthetic. Chimeric molecules comprising an antigen binding domain, or equivalent, fused to another polypeptide are therefore included. Cloning and expression of chimeric antibodies are described in EP-A-0120694 and EP-A-0125023.

Examples of antibody molecules include (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996). Antibody molecules and methods for their construction and use are described in Holliger & Hudson, *Nature Biotechnology* 23(9):1126-1136 (2005).

Where bispecific antibody molecules are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against IL-217BR, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996).

It is possible to take monoclonal and other antibodies and use techniques of recombinant DNA technology to produce other antibody molecules or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EPA-184187, GB 2188638A or EP-A-239400.

Preferably the CDR regions are grafted into a human framework region. The human framework region may be selected by a number of methods, e.g. by comparing the mouse framework region or mouse V region sequences with known human framework or V region sequences and selecting a human framework region which has the highest, or one of the highest degrees of amino acid similarity or identity. Modifications to framework regions of native human sequences may be made in order to further optimize the resulting CDR-grafted antibodies.

Although antibody molecules comprising a pair of VH and VL domains are preferred, single binding domains based on either VH or VL domain sequences may also be used. It is known that single immunoglobulin domains, especially VH domains, are capable of binding target antigens in a specific manner.

In the case of either of the single chain binding domains, these domains may be used to screen for complementary domains capable of forming a two-domain antibody molecule able to bind IL-17BR, as discussed further herein below.

Antibody molecules may further comprise antibody constant regions or parts thereof. For example, a VL domain may be attached at its C-terminal end to antibody light chain constant domains including human Cκ or Cλ chains, preferably Cλ chains. Similarly, an antibody molecule based on a VH domain may be attached at its C-terminal end to all or part of an immunoglobulin heavy chain derived from any antibody isotype, e.g. IgG, IgA, IgE and IgM and any of the isotype subclasses, particularly IgG1 and IgG4. IgG4 is preferred. Fc regions such as Δnab and Δnac as disclosed in WO99/58572 may be employed.

Framework regions of antibody molecules of the invention may also include glycosylation sequences that include one or more glycosylation sites. Depending upon the host cell in which the antibody is expressed, the pattern of glycosylation may vary. Thus nucleic acid constructs that encode glycosylation sites may be modified to remove the site or alternatively such sites may be introduced into the protein. For example, N-glycosylation sites in eukaryotic proteins are characterized by an amino acid triplet Asn-X-Y, wherein X is any amino acid except Pro and Y is Ser or Thr. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846.

The term "antigen-binding domain" describes the part of an antibody molecule which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) or at least a substantial portion thereof and an antibody heavy chain variable region (VH) or at least a substantial portion thereof.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibody molecules made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more detail below.

Antibody molecules and nucleic acid encoding antibody molecules will generally be isolated i.e. free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo.

Antibody molecules and nucleic acid may be formulated with diluents or adjuvants and still for practical purposes be isolated—for example the molecules will normally be mixed with gelatin or other carriers if used to coat microtitre plates for use in immunoassays, or will be mixed with pharmaceutically acceptable carriers or diluents when used in diagnosis or therapy. Antibody molecules may be glycosylated, either naturally or by systems of heterologous eukaryotic cells (e.g. CHO or NS0 (ECACC 85110503) cells), or they may be (for example if produced by expression in a prokaryotic cell) unglycosylated.

In addition to antibody sequences, an antibody molecule as described herein may comprise other amino acids, e.g. forming a peptide or polypeptide, such as a folded domain, or to impart to the molecule another functional characteristic in addition to ability to bind antigen.

In some embodiments, antibody molecules may carry a detectable or functional label, or may be conjugated to a toxin or enzyme (e.g. via a peptidyl bond or linker).

A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include radiolabels such as $^{131}$I or $^{99}$Tc, which may be attached to antibody molecules using conventional chemistry known in the art of antibody imaging. Labels also include enzyme labels such as horseradish peroxidase, alkaline phosphatase, glucose-6-phosphate dehydrogenase ("G6PDH"), alpha-D-galactosidase, glucose oxydase, glucose amylase, carbonic anhydrase and acetylcholinesterase. Labels include fluorescent labels or fluorescers, such as fluorescein and its derivatives, fluorochrome, rhodamine compounds and derivatives and GFP (GFP for "Green Fluorescent Protein"). Labels further include chemical moieties such as biotin which may be detected via binding to a specific cognate detectable moiety, e.g. labelled avidin.

Where the additional feature is a polypeptide domain or label, the antibody molecule may be produced by recombinant techniques, i.e. by the expression of nucleic acid encoding a fusion of the antibody molecule and the further domain.

Antibody molecules reactive with IL-17BR may comprise variants of the VH and VL domains and CDRs set out herein. Variants may be obtained by means of methods of sequence alteration or mutation and screening.

An antibody molecule according to the invention may also be one which competes for binding to IL-17BR with any antibody molecule which both binds IL-17BR and comprises a VH and/or VL domain disclosed herein, more preferably an antibody molecule comprising the VH domain of SEQ ID NO: 2 and the VL domain of SEQ ID NO: 4. Thus, a further aspect of the present invention provides an antibody molecule comprising a human antibody antigen-binding site which competes with D9.2 for binding to IL-17BR. Competition between antibody molecules may be assayed easily in vitro, for example using ELISA and/or by tagging a specific reporter molecule to one antibody molecule which can be detected in the presence of other untagged antibody molecule(s), to enable identification of antibody molecule(s) which bind the same epitope or an overlapping epitope.

Various methods are available in the art for obtaining antibody molecules against IL-17BR and which may compete with D9.2 for binding to IL-17BR.

Variants of the variable domain amino acid sequences disclosed herein may be employed, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, 4, 3, 2 or 1. Alterations may be made in one or more framework regions and/or one or more CDRs.

A CDR amino acid sequence substantially as set out herein may be carried as a CDR in a human variable domain or a substantial portion thereof. For example, VH CDR3 sequences substantially as set out herein may be carried as a VH CDR3 in a human heavy chain variable domain or a substantial portion thereof.

Another aspect of the invention provides an antibody molecule which binds IL-17BR and which comprises an antibody VH domain comprising a VH CDR3 substantially as set out in SEQ ID NO:7.

An antibody molecule may comprise a VH domain which comprises a VH CDR1, CDR2 and CDR3 substantially as set out in SEQ ID NOS: 5, 6 and 7, respectively.

A VH domain may be paired with a VL domain, for example a VL domain with a CDR1, CDR2 and CDR3 substantially as set out in SEQ ID NOS: 8, 9 and 10, respectively.

In some embodiments, an antibody molecule may comprise a VH domain which comprises a VH CDR1, CDR2 and CDR3 substantially as set out in SEQ ID NOS: 5, 6 and 7, respectively; and, a VL domain with a CDR1, CDR2 and CDR3 substantially as set out in SEQ ID NOS: 8, 9 and 10, respectively.

The VH and VL domains may have human or non-human framework regions, for example framework regions substantially as set out in the framework regions of SEQ ID NO: 2 and SEQ ID NO:4, respectively.

In some embodiments, the antibody molecule may comprise the VH and VL domain sequences substantially as set out in SEQ ID NO: 2 and SEQ ID NO:4, respectively.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

Sequence variants of antibody molecules may be generated by carrying out random mutagenesis of one or both of the D9.2 VH and/or VL genes to generate mutations within the entire variable domain. Such a technique is described by Gram et al (1992, Proc. Natl. Acad. Sci., USA, 89:3576-3580), who used error-prone PCR.

Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

All the above described techniques are known as such in the art and in themselves do not form part of the present invention. The skilled person will be able to use such techniques to provide antibody molecules as described herein using routine methodology in the art.

Accordingly, another aspect of the invention provides a method for obtaining an antibody molecule against IL-17BR which comprises:
  providing a starting nucleic acid encoding a antibody molecule that has one or more (i.e. one, two, three, four, five or all six) of the CDR sequences of SEQ ID NO:2 or SEQ ID NO:4;
  modifying said nucleic acid to alter the CDR sequence or sequences;
  expressing said modified antibody molecule; and
  testing said modified antibody molecule for binding against IL-17BR.

Preferably the modification will be performed on a plurality of starting nucleic acid molecules to provide a repertoire of modified sequences having a diversity of binding affinities.

The starting nucleic acid preferably comprises all three heavy chain CDRs of SEQ ID NO: 2, either in the form of SEQ ID NO:2 itself or carried in another framework sequence.

The modifications may be directed at a single CDR, e.g. the CDR3, or the modifications may be directed to two or three CDR regions simultaneously.

Variable domains employed in the invention may be obtained from any germ-line or rearranged human variable domain, or may be a synthetic variable domain based on consensus sequences of known human variable domains. A CDR sequence as described herein (e.g. CDR3) may be introduced into a repertoire of variable domains lacking a CDR (particularly CDR3), using recombinant DNA technology.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide antibody molecules as described herein. The repertoire may then be displayed in a suitable host system such as the phage display system of WO92/01047 so that suitable antibody molecules may be selected. A repertoire may consist of from anything from $10^4$ individual members upwards, for example from $10^6$ to $10^8$ or $10^{10}$ members.

Analogous shuffling or combinatorial techniques are also disclosed by Stemmer (Nature, 1994, 370:389-391), who describes the technique in relation to a β-lactamase gene but observes that the approach may be used for the generation of antibodies.

A further aspect of the invention thus provides a method of preparing an antibody molecule specific for IL-17BR, which method comprises:
  (a) providing a starting repertoire of nucleic acids encoding a VH domain which either include a CDR3 to be replaced or lack a CDR3 encoding region;
  (b) combining said repertoire with a donor nucleic acid encoding an amino acid sequence substantially as set out in SEQ ID NO:7 such that said donor nucleic acid is inserted into the CDR3 region in the repertoire, so as to provide a product repertoire of nucleic acids encoding a VH domain;
  (c) expressing the nucleic acids of said product repertoire;
  (d) selecting a antibody molecule specific for a IL-17BR; and
  (e) recovering said antibody molecule or nucleic acid encoding it.

The product repertoire may be co-expressed, from the same vector or different vector, with a VL domain. The VL domain may be a VL domain described herein e.g. the VL domain of SEQ ID NO: 4, or may be one or more different VL domains, as described below in relation to chain shuffling.

An analogous method may be employed in which a VL CDR3 substantially as set out in SEQ ID NO: 10 is combined with a repertoire of nucleic acids encoding a VL domain which either include a CDR3 to be replaced or lack a CDR3 encoding region. As with the method above, the VL product repertoire may be co-expressed, from the same vector or different vector, with a VH domain. The VH domain may be a VH domain described herein i.e. the VH domain of SEQ ID NO: 2 or may be one or more different VH domains, as described below in relation to chain shuffling.

Similarly, one or more, or all three CDRs may be grafted into a repertoire of VH or VL domains which are then screened for an antibody molecule or antibody molecules specific for IL-17BR.

Antibody molecules obtained in this manner form a further aspect of the invention.

Another aspect of the invention provides a method for obtaining an antibody antigen-binding domain for IL-17BR, the method comprising combining a VH domain of an antibody molecule described herein (including variants as discussed above) with one or more VL domains, and testing the VH/VL combination or combinations for antibody-antigen binding domain for IL-17BR.

Said VL domain may have an amino acid sequence which is substantially as set out herein. For example, the VL domain may be substantially as set out in SEQ ID NO: 4.

An analogous method may be employed in which one or more sequence variants of a VL domain disclosed herein are combined with one or more VH domains.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain antibody molecule is selected in accordance with phage display techniques such as those described in that reference.

Another aspect of the present invention provides a method for selection of an antibody molecule for IL-17BR, the method comprising:
  (a) providing an antibody VH domain comprising a VH CDR3 with the amino acid sequence of SEQ ID NO. 7;
  (b) combining said VH domain with a plurality of antibody VL domains to provide antibody molecules;
  (c) screening said antibody molecules for binding to IL-17BR; and
  (d) selecting an antibody molecule which binds IL-17BR.

In such a method, the VH and VL domains may be provided in the form of proteins expressed by recombinant DNA, particularly by a phage or phagemid DNA.

The plurality of VL domains may be anything from $10^4$ individual domains upwards, for example from $10^6$ to $10^8$ or $10^{10}$ domains.

IL-17BR, also referred to in the art as IL-25R, IL-17RB or IL-17RH1, is available from commercial sources (e.g. R&D Systems, MN, USA) as an Fc-fusion protein, or may be cloned or synthesised by reference to the sequences of IL-17BR available in the art.

Murine IL-17BR (GeneID: Nucleic acid: NM_019583.3 GI:142368701; NP_062529.2 GI:83025064) is described by Tian et al., 2000 (Ref. 11 below). Human IL-17BR (GeneID: 55540, Nucleic acid: NM_018725.3 GI:112382255; Protein NP_061195.2 GI:27477074) is described by Shi, Y., et al., 2000 (Ref. 10 below).

For production of antibodies or use in immunoassays, fragments of recombinant IL-17BR may be used, particularly those containing the extracellular domain.

In further aspects, the invention provides an isolated nucleic acid which comprises a nucleotide sequence encoding an antibody molecule, a VH domain, or a VL domain as described above, for example a VH or VL domain of SEQ ID NOS: 2 and 4 respectively, and methods of preparing an antibody molecule, a VH domain, or a VL domain as described above, which comprise expressing said nucleic acid under conditions to bring about production of said antibody molecule, VH domain, or VL domain, and recovering it.

Another aspect of the present invention provides nucleic acid, generally isolated, encoding a VH CDR or VL CDR sequence disclosed herein, especially a VH CDR selected from SEQ ID NOs: 5, 6 and 7, a VL CDR selected from SEQ ID NOs: 8, 9 and 10, most preferably D9.2 VH CDR3 (SEQ ID NO. 7).

The nucleic acids of the invention may comprise the sequences, or relevant portions thereof (e.g. CDR-encoding regions) of SEQ ID NO:1 or SEQ ID NO:3, or variants of these sequences modified by, for example, site-directed mutagenesis to encode other VH and VL domains of the invention. However, codon usage may be varied, e.g. to optimize expression of the sequence in a desired host cell.

Another aspect of the present invention provides an isolated nucleic acid encoding an antibody molecule of the present invention. Nucleic acid includes DNA and RNA. In a preferred aspect, the present invention provides a nucleic acid which encodes a CDR or a VH or VL domain of the invention as defined above.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Aspects of the present invention also provide vectors, for example in the form of plasmids, viruses, e.g. phage, or phagemid, cosmids, transcription or expression cassettes which comprise at least one nucleic acid as above.

Suitable vectors can be chosen or constructed, containing appropriate regulatory sequences, including promoter sequences, terminator sequences, polyadenylation sequences, enhancer sequences, marker genes and other sequences as appropriate. For further details see, for example, Molecular Cloning: a Laboratory Manual: 2nd edition, Sambrook et al., 1989, Cold Spring Harbor Laboratory Press. Vectors also include viral vectors capable of infecting human cells in vivo, e.g. adenoviral, retroviral or adeno-associated virus vectors. Such vectors may be useful for expression of an antibody molecule of the invention in the cells of a human or animal subject, to provide for production and delivery of the antibody molecule to said subject.

A nucleic acid sequence encoding an antibody molecule of the invention will in one aspect be operably linked to a promoter to effect expression of the antibody molecule in a host cell. The sequence may include at its 5' end a leader sequence to facilitate expression and/or secretion of the antibody molecule in and/or from a host cell. Numerous suitable leader sequences are known as such in the art and may be selected by a person of ordinary skill in the art taking account of the host cell.

Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds. John Wiley & Sons, 1992. The disclosures of Sambrook et al. and Ausubel et al. are incorporated herein by reference.

Another aspect provides a host cell transformed with a nucleic acid (e.g. a nucleic acid sequence in the form of a vector) of the invention.

Nucleic acid may be integrated into the genome (e.g. chromosome) of the host cell. Integration may be promoted by inclusion of sequences which promote recombination with the genome, in accordance with standard techniques.

Another aspect provides a method of production of an antibody molecule as described herein, the method including causing expression from encoding nucleic acid. Such a method may comprise culturing host cells under conditions for production of said antibody molecule.

Following production by expression, a VH or VL domain, or antibody molecule may be isolated and/or purified using any suitable technique, then used as appropriate. A method of production may comprise a step of isolation and/or purification of the product.

Following purification of the product the antibody molecule may be modified by physical or chemical means, for example to introduce protective groups that alter, e.g. increase, the stability or biological half-life of the protein. For example, PEGylation of proteins to achieve such effects is known as such in the art and antibody molecules of the invention may be in PEGylated form.

A method of production may comprise formulating the product into a composition including at least one additional component, such as a pharmaceutically acceptable excipient.

The present invention also provides a recombinant host cell which comprises one or nucleic acids or vectors as above.

Systems for cloning and expression of an antibody molecule in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells, YB2/0 rat myeloma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of an antibody molecule, see for recent reviews, for example Ref, M. E. (1993) Curr. Opinion Biotech. 4: 573-576; Trill J. J. et al. (1995) Curr. Opinion Biotech 6: 553-560.

The data set out herein shows for the first time that antibodies against IL-17BR are effective in preventing or reducing airway hyperresponsiveness in vivo, a key symptom of asthma.

Another aspect of the invention provides a method of preventing or reducing airway hyperresponsiveness in a subject (e.g. a human) in need thereof which comprises administering to the subject an antibody molecule which binds IL-17BR, for example an antibody molecule described above. Another aspect of the invention provides a method of preventing, reducing or treating asthma or other IL-25 mediated condition in a subject in need thereof which comprises administering to the subject an antibody molecule that binds IL-17BR. Other IL-25 mediated conditions include allergy and colitis, which includes ulcerative colitis and Crohn's disease. Asthma includes allergic asthma.

Accordingly, another aspect of the invention provides a method of preventing or reducing inflammation of the colon in a subject (e.g. a human) in need thereof, which comprises administering to the subject an antibody molecule that binds IL-17BR, for example an antibody molecule described above. Another aspect of the invention provides a method of preventing, reducing or treating IBD, which comprises administering to the subject an antibody molecule that binds IL-17BR. IL-25 mediated conditions include ulcerative colitis and Crohn's disease. Other IL-25 mediated conditions include colitis (inflammation of the colon), including chronic colitis.

The above methods may be practiced with antibody molecules (including compositions thereof) as described above, which are useful in binding to IL-17BR and antagonising the effects of IL-17BR/IL-25 binding, with therapeutic potential in various diseases and disorders in which IL-17BR plays a role. The methods may also be practiced with other antibody molecules (including compositions thereof) which bind IL-17BR and antagonise the effects of IL-17BR/IL-25 binding, which may be obtained as described below in the accompanying examples.

Antibody molecules (including compositions thereof) described, above may be used in a method of treatment (including prophylactic treatment) or diagnosis in human or animal subject. Such a method of treatment or diagnosis (which may include prophylactic treatment) may comprise administering to said subject an effective amount of an antibody molecule of the invention. Exemplary diseases and disorders are discussed further below.

Also provided is the use of an antibody molecule (including a composition thereof) described herein in the manufacture of a medicament for administration, to a human or animal subject.

Clinical indications in which an anti-IL-17BR antibody molecule may be used to provide therapeutic benefit include any condition in which IL-17BR/IL-25 binding has pathological consequences. Thus in general, the antibody molecule described herein may be used in the treatment of any IL-25 mediated condition, for example associated with an unwanted Th2 response or type-2 responses. In some embodiments, the antibody molecule of the invention may be used for the treatment of allergy and asthma, particularly asthma. In some embodiments, the antibody molecule of the invention may be used for the treatment of IBD, particularly the treatment of UC and/or CD.

Anti-IL-17BR treatment may be given by injection (e.g. intravenously) or by local delivery methods. Anti-IL-17BR may be delivered by gene-mediated technologies. Alternative formulation strategies may provide preparations suitable for oral or suppository route. The route of administration may be determined by the physicochemical characteristics of the treatment, by special considerations for the disease, to optimise efficacy or to minimise side-effects.

The compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg-1.0 g, and this may be administered intravenously as a bolus or as an infusion over several hours as appropriate to achieve the required dose. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

A further mode of administration employs precoating of, or otherwise incorporation into, indwelling devices, for which the optimal amount of antibody will be determined by means of appropriate experiments.

An antibody molecule in some embodiments may be a monomeric fragment, such as F(ab) or scFv. Such antibody fragments may have the advantage of a relatively short half life and less risk of platelet activation, which may be caused by receptor clustering. Clustering which gives rise to platelet activation could be either of IL-17BR molecules or of IL-17BR with FcγRII molecules, for instance.

If a whole antibody, is used, it is preferably in a form that is unable to activate and/or destroy platelets. The IgG4 isotype or alternatively "designer" isotypes derived from the IgG1 backbone (novel Fc gene constructs WO99/58572, Clark, Armour, Williamson) are preferred choices. Smaller antibody fragments may be used, such as F(ab')$_2$. In addition, whole antibodies or fragments (e.g. F(ab')$_2$ or diabodies) with dual epitope specificity (e.g. for the epitopes recognised by scFv D9.2) may be used. Although such an embodiment may promote receptor clustering, a high association rate to individual receptors may rule out this problem.

Antibody molecules described herein will usually be administered in the form of a pharmaceutical composition, which may comprise at least one component in addition to the antibody molecule.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Therapeutic formulations of the antibody molecule may be prepared for storage by mixing the antibody molecule having the desired degree of purity with optional physiologically acceptable carriers, excipients, or stabilizers (see e.g. "Remington: The Science and Practice of Pharmacy", 20th Edition, 2000, pub. Lippincott, Williams & Wilkins.), in the form of lyophilized powder or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

For the antibody molecule to be used for in vivo administration it must be sterile. This is readily accomplished by filtration through sterile filtration membranes, prior to or following lyophilization and reconstitution. The antibody molecule ordinarily will be stored in lyophilized form or in solution.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

An antibody molecule of the invention may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine; the administration of anti-emetics; or the administration of at least one other compound active against asthma, generally a bronchodilating agent which produces airway relaxation or enhances mucus clearance, e.g. a beta-agonist (e.g. salbutamol, salmeterol), disodium cromoglycate, steroids or an inhibitor of $PDE_{IV}$.

Another aspect of the invention provides a method comprising causing or allowing binding of an antibody molecule as provided herein to IL-17BR. As noted, such binding may take place in vivo, e.g. following administration of an antibody molecule, or nucleic acid encoding an antibody molecule, or it may take place in vitro, for example in ELISA, Western blotting, immunocytochemistry, immuno-precipitation or affinity chromatography.

The amount of binding of antibody molecule to IL-17BR may be determined. Quantitation may be related to the amount of the antigen in a test sample, which may be of diagnostic interest.

The reactivities of antibody molecules on a sample may be determined by any appropriate means. Radioimmunoassay (RIA) is one possibility. Radioactive labelled antigen is mixed with unlabelled antigen (the test sample) and allowed to bind to the antibody molecule. Bound antigen is physically separated from unbound antigen and the amount of radioactive antigen bound to the antibody determined. The more antigen there is in the test sample the less radioactive antigen will bind to the antibody molecule. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of an antibody molecule as above for measuring antigen levels in a competition assay, that is to say a method of measuring the level of antigen in a sample by employing an antibody molecule as provided herein in a competition assay. This may be where the physical separation of bound from unbound antigen is not required. Linking a reporter molecule to the antibody molecule so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing an antibody molecule as described herein for example in a biosensor system.

The mode of determining binding is not a feature of the present invention and those skilled in the art are able to choose a suitable mode according to their preference and general knowledge.

The present invention further extends to an antibody molecule which competes for binding to IL-17BR with any antibody molecule which both binds the antigen and comprises a VH and/or VL domain including a CDR with amino acid substantially as set out herein or a VH and/or VL domain with amino acid sequence substantially as set out herein. Competition between antibody molecules may be assayed easily in vitro, for example by tagging a specific reporter molecule to one antibody molecule which can be detected in the presence of other untagged antibody molecule(s), to enable identification of antibody molecules which bind the same epitope or an overlapping epitope. Competition may be determined for example using ELISA or flow cytometry.

A competition reaction may be used to select one or more antibody molecules such as derivatives of D9.2, which may have one or more additional or improved properties. This is analogous to the selection method for D9.2 in accordance with the invention, except that IL-17BR is not eluted from its mini-ligand but from an antibody molecule. This may be important as it should yield a greater proportion of daughter antibody molecules which directly compete with the parent. Indeed such daughter antibody molecules as are selected may have a greater affinity for the antigen than the parent (allowing for enhancements in avidity which may result from the display of more than one antibody molecule per phage). Current methods of selecting for "daughter" phage antibody molecules of improved affinity include:

using concentrations of (labelled) target antigen lower than the dissociation constant of the original parent antibody;

using excess unlabelled target antigen as a competitor as demonstrated in Hawkins et al. (1992). However, they do not necessarily specify that the "improved" antibody must displace/occupy the same epitope as the parent. Incorporating the elution step should yield a higher proportion of daughter antibody molecules which do displace the parent. Daughter antibody molecules selected in this way may bind a very similar epitope to the parent antibody molecule, but with a greater affinity.

In testing for competition a peptide fragment of IL-17BR may be employed, especially a peptide including an epitope of interest. A peptide having the epitope sequence plus one or more amino acids at either end may be used. Such a peptide may be said to "consist essentially" of the specified sequence. Antibody molecules according to the present invention may be such that their binding for IL-17BR is inhibited by a peptide with or including the sequence given. In testing for this, a peptide with either sequence plus one or more amino acids may be used.

Antibody molecules which bind a specific peptide may be isolated for example from a phage display library by panning with the peptide(s).

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Materials and Methods
Screening Supernatants by ELISA 96-well immunoplates (Nunc) were coated with 50 μl/well murine or human IL-17Br-Fc fusion protein at 1 μg/ml in 0.1 M NaHCO$_3$ overnight at 4° C. or for 3 hrs at room temperature. The next day, wells were washed 5 times with PBS 0.05% tween and then blocked in PBS 10% FCS for 4 hrs at room temperature. For the same 4 hour period, supernatants from hybridoma cell culture were incubated with 50 μg/ml hIgG. This was to block any antibodies in the supernatants that had been raised against the Fc portion of the fusion protein. Supernatants that did not receive this treatment were also included in the ELISA to give an indication of the amount of anti-Fc antibody in each sample.

Following the 4 hour blocking step, immunoplates were washed 5 times in PBS 0.05% tween and supernatants were added neat, at 50 μl/well. Supernatants were left on the plate overnight at 4° C. or for 3 hrs at room temperature before the wells were washed 5 times in PBS 0.05% tween. 50 μl of 0.5 μg/ml anti-mouse immunoglobulins-HRP (DAKO) in PBS 10% FCS was added to each well and left for one hour at room temperature before a final 8 washes in PBS 0.05% tween were performed. Bound antibody was detected with an ELISA development solution and the A405 recorded on a Tecan immunoplate reader.

To distinguish antibodies raised against the Fc portion of the fusion protein from those directed against IL-17BR, control plates were coated with hIgG and supernatants were added following the protocol above. Samples that gave a high A405 on hIgG coated plates were not considered for further study.

Flow Cytometry Screening of Transfected COS7 Cells cDNAs for the murine and human IL-17BR genes were separately cloned into the pME18S expression vector and termed mIL17BR-pME18S and hIL17BR-pME18S respectively.

$2\times10^6$ COS7 cells in DMEM 10% FCS were plated onto a 10 cm dish and incubated overnight at 37° C. The following day, 4 μg mIL17BR-pME18S or hIL17BR-pME18S was mixed with 10 μl lipofectamine in 500 μl serum free Optimem and incubated at room temperature for 30 minutes before being added onto the plated cells. Cells were then incubated at 37° C. for 6 hrs before adding fresh media. Cells were harvested for FACS analysis 48 hrs post-transfection.

For FACS analysis, transfected or non-transfected cells were incubated with candidate anti-IL17BR antibodies at varying concentrations in PBS 2% FCS for 30 minutes. Cells were then washed before incubation with anti-mouse IgG FITC (BD Pharmingen) at 2 μg/ml in PBS 2% FCS for a further 30 minutes. Finally, cells were washed twice in PBS 2% FCS and analysed for IL-17Br expression on a Becton Dickinson FACScalibur machine.

D9.2 Cross-Reactivity

ELISA plates were coated with IL-17R-family members; IL-17RA, IL-17BR, IL-17RC, or IL-17RD, or IL-13Rα control (R&D Systems) at 2 μg/ml overnight at 4° C. before washing in PBS/0.05% tween and blocking in PBS/10% FCS at room temperature for 4 hrs. Biotinylated D9.2 was added at 1 μg/ml in PBS/10% FCS and incubated overnight at 4° C. Plates were then washed before streptavidin-HRP was added and incubated for 1 hr at room temperature. Plates were then washed a final time before adding ELISA development solution and measuring the absorbance at 405 nm.

Mouse Monoclonal Antibody—Human IL-17BR Binding Assay

Human IL-25 (hIL17e)(R&D sys) was coated onto a Nunc Maxisorp microwell plate at 0.5 μg/ml and incubated for 1 hour 30 mins at room temperature. The plate was washed three times and then blocked with Tris/1% BSA for 1 hour. hIL17Br/Fc chimeric (R&D sys) was diluted to 100 ng/ml. Each purified mouse monoclonal antibody was diluted (×100) in hIL17Br/Fc (100 ng/ml) to a final concentration of 1 μg/ml in a hIL17Br/Fc solution at 100 ng/ml. The [antibody×hIL17Br/Fc] mix was incubated 1 hour 30 mins at room temperature. The [antibody×hIL17Br/Fc] mix was added to the hIL17e-coated plate and incubated 1 hour 30 mins before being washed three times. Anti-hIgG (Fc)-HRP conjugate (Serotec) was added to the plate and incubated for 45 mins at RT before being washed three times and developed with TMB. Reaction was stopped with 1 M HCL. Optical density was read at 450 nm, and the reagent blank reading subtracted from all readings.

IL-17BR/IL25 Inhibition Assay

Mysenteric lymph nodes were removed from naïve BALB/c mice and passed through 70 μm cell-strainers to achieve a single-cell suspension. Cells were washed in PBS 2% FCS and then T-cells and B-cells were depleted. This was achieved by incubating cells with biotinylated anti-CD19 and anti-CD3 antibodies at 5 μg/ml, on ice, for 30 minutes and then incubating with anti-biotin Dynabeads (Invitrogen) at a concentration of 4 beads per cell for 20 minutes at 4° C. The mixture was then washed before being passed over a magnet to separate labelled T- and B-cells from the unlabelled non-B non-T (NBNT) cell fraction. Purity of the NBNT fraction was tested by FACS, staining for B220, CD4 and CD8.

NBNT cells were then plated on round bottomed 96-well plates at $3 \times 10^5$ cells/well and incubated for 72 hrs in RPMI 10% alone or RPMI 10% FCS with 10 ng/ml IL-25. Candidate IL-17BR blocking antibodies were added to wells in serial dilution from a top concentration of 2 μg/ml and incubated for 1.5 hrs before addition of 10 ng/ml IL-25 to the wells. Plates were then incubated at 37° C. for 72 hrs before supernatants were harvested and tested for IL-13 protein content by Quantikine ELISA (R&D systems).

For CD4+ (T and/or NKT) cells, spleens were taken from naïve wild-type BALB/c mice and a single cell suspension prepared. Red blood cell lysis was performed before washing cells in MACS buffer (Miltenyi Biotec). CD4+ cell isolation was carried out by positive selection using CD4 MicroBeads (Miltenyi Biotec) according to manufacturers instructions. CD4+ cells were then cultured at $1 \times 10^6$ cells/ml in 96-well plates either in RPMI alone or in RPMI supplemented with 10 ng/ml IL-25 with or without D9.2 at 1 μg/ml. Cells were cultured for 72 hrs and then supernatants taken for analysis of IL-13 protein levels by Quantikine ELISA (R&D systems).

Renal Carcinoma Cell Line Bioassays

Human TK-10 renal carcinoma cells were obtained from the National Cancer Institute (NCI). RENCA cells were obtained from Cell Biology services, Centocor R&D. Both cell lines were maintained in DMEM growth medium with 10% FCS at 37° C., 5% $CO_2$ in a humidified atmosphere. Cells were plated in 96-well flat bottom tissue culture treated plates at a density of $2.5 \times 10^4$ cells/well in a total volume of 100 μl complete growth medium. Following overnight incubation, the cells were washed with 1×PBS and then incubated with 100 ng/ml of IL-25 and 10 ng/ml TNF-α in OptiMEM reduced serum medium, or medium only control, for 24 hr. Cell supernatant was collected 20-24 hrs post IL-25 stimulation and stored at −20° C. for subsequent analysis of soluble KC/IL-8 release using a mouse Quantikine ELISA for KC or human Quanitkine ELISA for IL-8 (R&D systems).

D9.2 or IgG1 control were tested for ability to prevent IL-25-mediated IL-8 (KC) release. For inhibition experiments, a constant amount of IL-25 (100 ng/ml) was pre-incubated with varying concentrations of D9.2 or anti-c-myc mouse IgG1 (clone 9E10.2) control antibody for 30-60 minutes at room temperature prior to addition to the respective cells. TNF-α (10 ng/ml) was added to the cells immediately prior to addition of the IL-25 protein/D9.2. Determination of IL-8 (KC) release was performed at 24 hr post stimulation as described above.

Mice

BALB/c mice for use in the experimental model of allergic asthma were obtained from Harlan UK, and BALB/c mice for use in the experimental model of IBD were obtained from Charles River. Mice were maintained in the SABU/CBS/Ares-MRC or National Heart and Lung Institute facilities in specific pathogen free environments. All animal experiments outlined in this report were undertaken with the approval of the UK Home Office.

Sensitisation and Allergen Exposure

For the experimental model of allergic asthma, BALB/c mice wild-type mice or IL-17BR knock-out mice on a BALB/c background were sensitised by intraperitoneal administration of OVA (20 μg/injection) complexed with alum, or 1:1 PBS:alum (controls), at days 0 and 12. Aerosol administration of PBS or 1% OVA was undertaken on days 19, 20, 21 for 20 minutes per day. On day 22 the animals were sacrificed and tissues collected.

For the experimental model of IBD, BALB/c mice were sensitized by skin application of a 4% (w/v) solution of oxazolone (OXA) in 100% ethanol or ethanol alone (controls), at day 0. Intra-rectal administration of a 3% (w/v) solution of oxazolone in 50% ethanol or 50% ethanol alone (controls) was performed at day 7. On day 9 the animals were sacrificed and tissues collected.

Administration of Anti-IL-17BR Antibodies

In the experimental model of allergic asthma, for mice receiving antibody treatment, an intraperitoneal injection of 250 μg D9.2 or anti-c-myc mouse IgG1 control antibody (clone 9E10.2) in PBS was given two hrs prior to each nebulisation. Each mouse received three doses of antibody.

In the experimental model of IBD, for mice receiving antibody treatment, an intraperitoneal injection of 500 μg of D9.2 or anti-KLH mouse IgG1 control antibody in PBS was given 24 hours prior to sensitization (day −1) and challenge (day 6). Thus each mouse received two doses of antibody.

Assessing AHR

Figure 8:
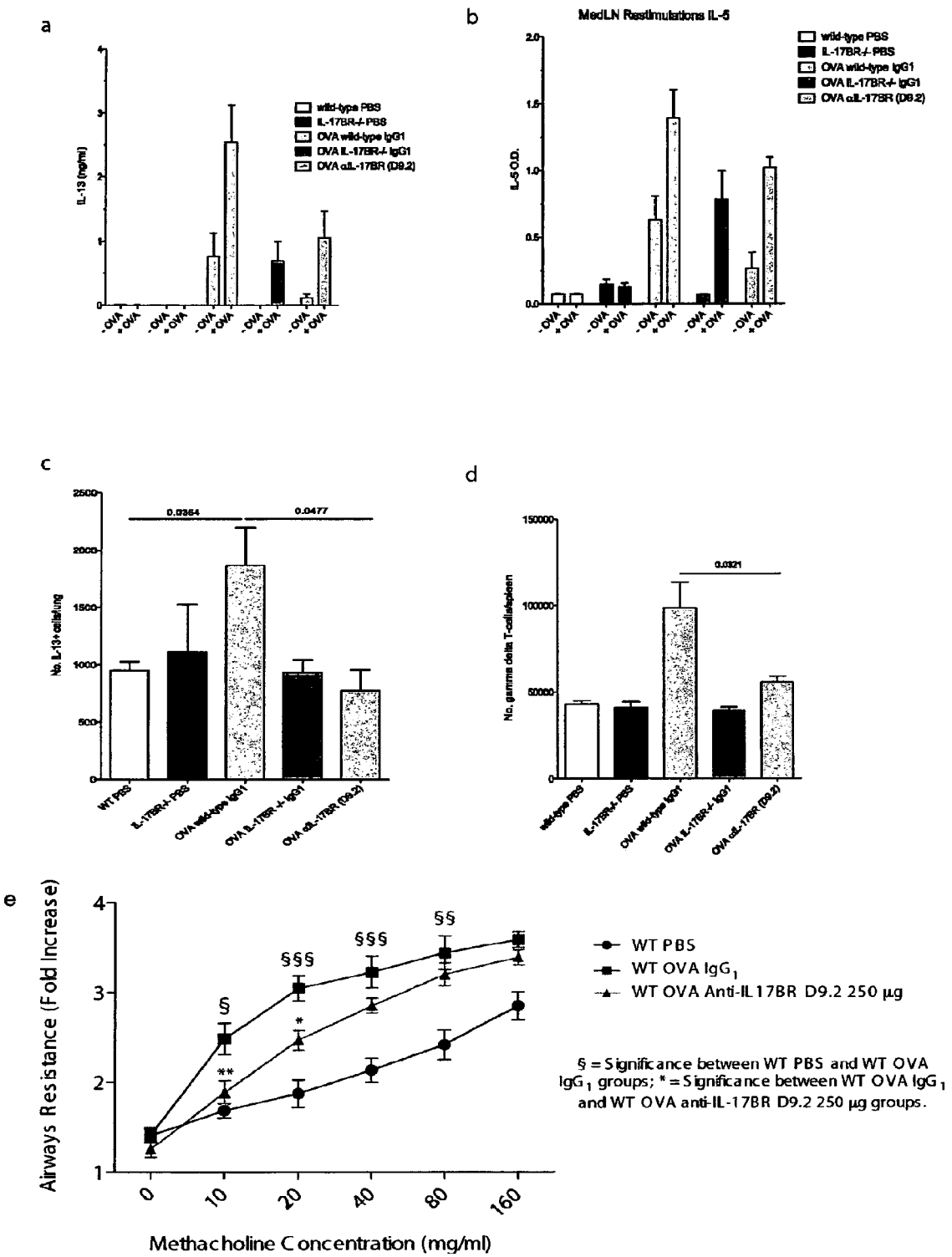
FIG. 8 shows that D9.2 blocks IL-25 responses in vivo. (a) Mediastinal lymph node cells from ovalbumin (OVA) sensitised and challenged mice produce IL-13 when restimulated with OVA in vitro. Administration of D9.2 prior to OVA challenge reduces the IL-13 response to levels comparable with those of IL-17BR KO mice. (b) Mediastinal lymph node cells from OVA sensitised and challenged mice produce IL-5 when restimulated with OVA in vitro. Administration of D9.2 prior to OVA challenge reduces the IL-5 response to levels comparable with those of IL-17BR KO mice. (c) D9.2 treatment reduced the number of IL-13-producing cells in the lung of OVA sensitised and challenged mice. Intracellular cytokine staining of IL-13 reveals a population of IL-13-producing cells in OVA sensitised and challenged mice which is absent in IL-17BR KO mice and is reduced in animals treated with anti-IL-17BR antibody D9.2 prior to OVA challenge. (d) Gamma-delta T-cell numbers in the spleen of OVA sensitised and challenged mice are reduced in IL-17BR KO mice and in mice given D9.2 prior to OVA challenge. (e) D9.2 treatment reduces AHR in OVA sensitised and challenged mice.

For FIG. 8(e), mice were sensitised by intraperitoneal (i.p.) administration of endotoxin-low ovalbumin and challenged daily for 6 days by nebulisation with aerosolised PBS (control) or OVA.

Mice receiving D9.2 antibody treatment were given an intraperitoneal injection of 250 μg D9.2 or anti-c-myc mouse IgG1 control antibody (clone 9E10.2) in PBS 2 hours prior to each of the last 3 nebulisations. 24 hours after the final aerosol challenge AHR was assessed using a restrained whole body plethysmograph (EMMS, UK). Animals were anaesthetised, tracheostomised, and ventilated (MiniVent 845 ventilator, EMMS, UK) at a rate of 175 breaths/min, with a tidal volume of 200 μl/stroke. After recording stable baseline pulmonary resistance for 3 mins increasing concentrations of acetyl-β-methylcholine chloride (methacholine) (Sigma-Aldrich) were administered by aerosol for 10 sec with an ultrasonic nebuliser, and pulmonary resistance was recorded for a 3 min period. eDaq software was used to analyse airways resistance, compliance, and standard pulmonary parameters.

Mediastinal Lymph Node Restimulations

Mediastinal lymph nodes from PBS- or OVA-treated mice were pushed through 70 μm cell-strainers to achieve a single cell suspension. Cells were counted and plated at $3 \times 10^5$ cells/well on round-bottomed 96-well plates. Cells were cultured for 72 hrs in RPMI 10% FCS alone or in the presence of 100

μg/ml OVA. Supernatants were then collected and assayed for IL-13 concentration using a Quantikine ELISA kit (R&D Systems).

Assessing IBD

Figure 9:
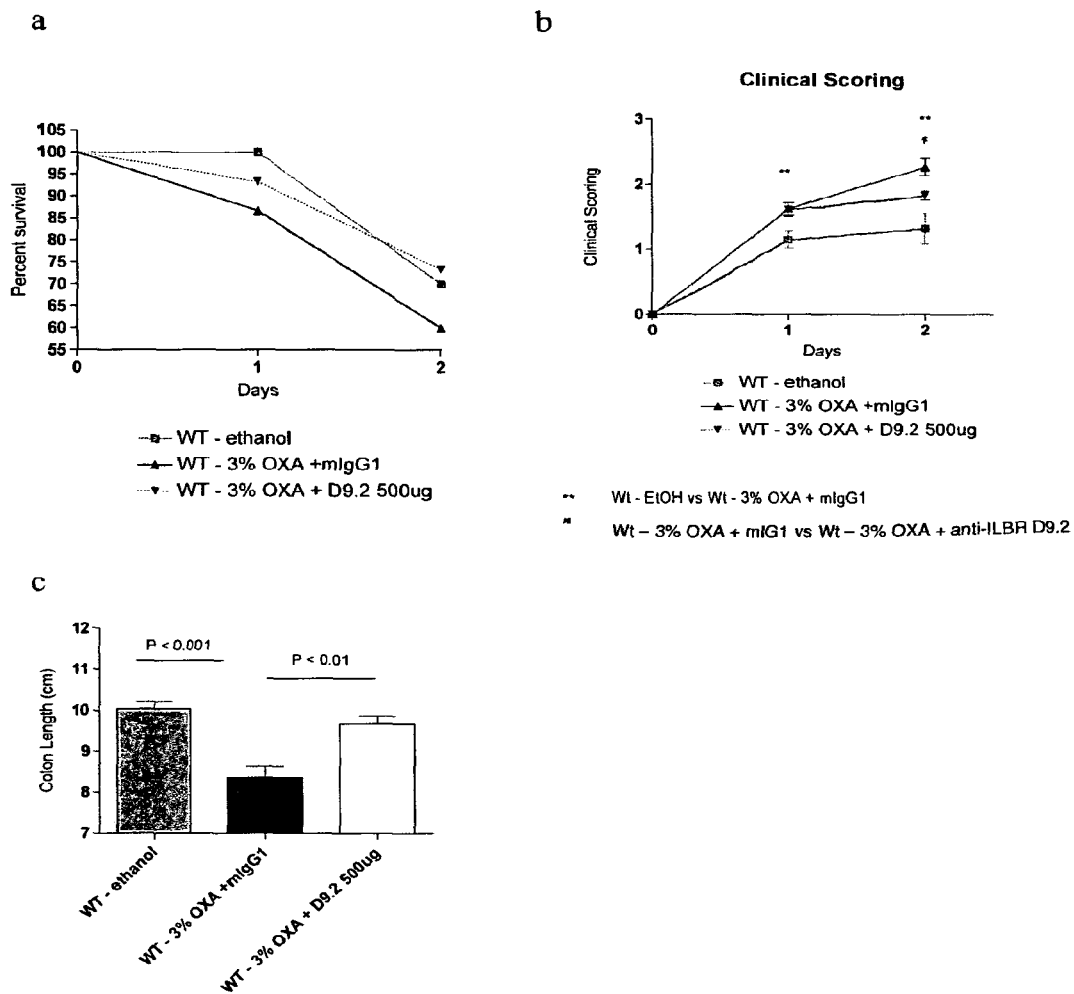
FIG. 9 shows that D9.2 blocks IL-25 responses in vivo in a mouse model of IBD. (a) Percentage survival of animals challenged with oxazolone is lower than controls, receiving only ethanol. Administration of D9.2 prior to sensitization and challenge reduces the mortality rate. (b) Clinical Scores are calculated based on weight loss in combination with the general appearance and behaviour of each animal. D9.2 administration results in an improvement of the clinical score in comparison to mice receiving isotype antibody. (c) Colon length is reduced in IBD mice compared with controls. D9.2 administration protects against this reduction in the IBD animals.

For FIG. 9, mice were sensitised by skin application of a solution of oxazolone in ethanol at day 0, and challenged with a solution of oxazolone in ethanol at day 7. Controls received ethanol alone. Mice receiving antibody treatment were given an intraperitoneal injection of D9.2 or anti-KLH mouse IgG1 antibody (control) at day −1 and day 6. At day 9, animals were sacrificed and tissues collected. (In FIGS. 9(a) and 9(b), days 7, 8 and 9 are numbered as days 0, 1 and 2 respectively.)

At days 7, 8 and 9, mice were weighed and their general appearance and behaviour assessed in order to assign a clinical score from 0 to 3 for each animal, based on the method described in Wang et al., 2004, the clinical score at day 7 being set at 0 (FIG. 9b). At day 9, mice were sacrificed and the colon of each mouse recovered, inspected and measured (FIG. 9(c)).

Example 1

Generation of Antibodies Against IL-17BR

We initially attempted to generate antibodies by immunising mice with synthetic peptides derived from the amino acid sequence of human IL-17BR. Despite generating monoclonal anti-peptide antibodies we failed to produce antibodies that would recognise the mature human IL-17BR protein. We then attempted to generate antibodies against a fusion protein of the human IL-17BR protein by immunising wild-type mice. Despite multiple immunisations and hybridoma fusions, we failed to generate high affinity antibodies against IL-17BR.

Mice also express a form of IL-17BR and we hypothesised whether our inability to raise a useful antibody was constrained by the lack of novel epitopes between the mouse and human IL-17BR molecules. We generated an IL-17BR-deficient mouse line that would no longer express IL-17BR. The IL-17BR-deficient mice were designed to remove all forms of IL-17BR including alternatively spliced variants. The high degree of conservation of the binding interface between human and mouse IL-17BR may reduce the likelihood of raising blocking antibodies in wild-type mice, so removing endogenous IL-17BR may facilitate the development of antibodies against the ligand binding site of the IL-17BR. This strategy also increased the possibility of raising an antibody to IL-17BR that would block the binding of both mouse and human IL-25. This is useful since cross-reactive antibodies can be tested for efficacy in mouse models of disease.

After generation and characterisation of IL-17BR-deficient animals, immunisation with IL-17BR-Fc fusion protein was performed. This strategy did prove more successful than using wild-type mice but still required the screening of large numbers of hybridomas in order to identify candidate antibodies.

Figure 2:
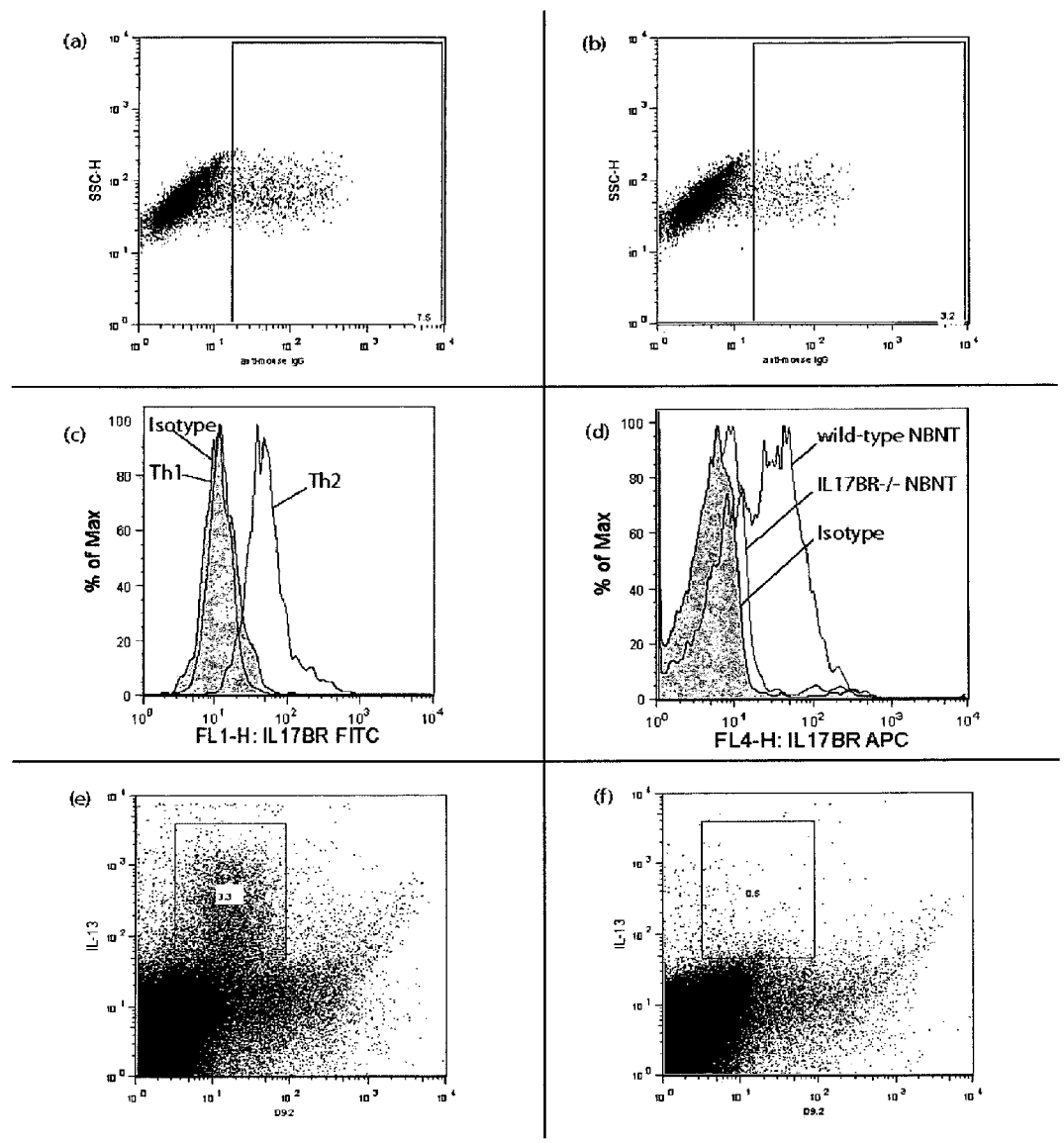
FIG. 2 shows D9.2 binds IL-17BR on transfected COS7 cells and on primary mouse cells. COS7 cells transfected with murine (a) or human (b) IL-17BR expression vectors express IL-17BR that is recognised by D9.2. Cells were incubated with 1 µg/ml D9.2 for 20 minutes and then washed. D9.2 binding was detected by FACS after 20 minute incubation with anti-mouse IgG FITC at 0.5 µg/ml. (c) In vitro differentiated Th2 cells express IL-17BR and are bound by D9.2. Expression is low or absent on Th1 cells. (d) After three consecutive daily intraperitoneal doses of 400 ng IL-25, a population of 1'-17BR-expressing non-B non-T (NBNT) cells appears in the mysenteric lymph node of wild-type (d, e) but not IL-17BR knock-out (d, f) mice. This population is recognised by D9.2 and produces IL-13.

A large panel of antibodies, generated in il17br$^{-/-}$ mice immunized against mouse IL-17BR-Fc fusion protein, was screened for binding to human and mouse IL-17BR by ELISA. One of the anti-IL-17BR antibodies identified (D9.2) bound well to both murine and human IL-17BR by ELISA (FIG. 1) as well as to both native mouse and human IL-17BR protein expressed on COS cells transfected with mouse IL-17BR cDNA or human IL-17BR cDNA (FIG. 2).

Example 2

In Vitro Testing of D9.2

Figure 3:
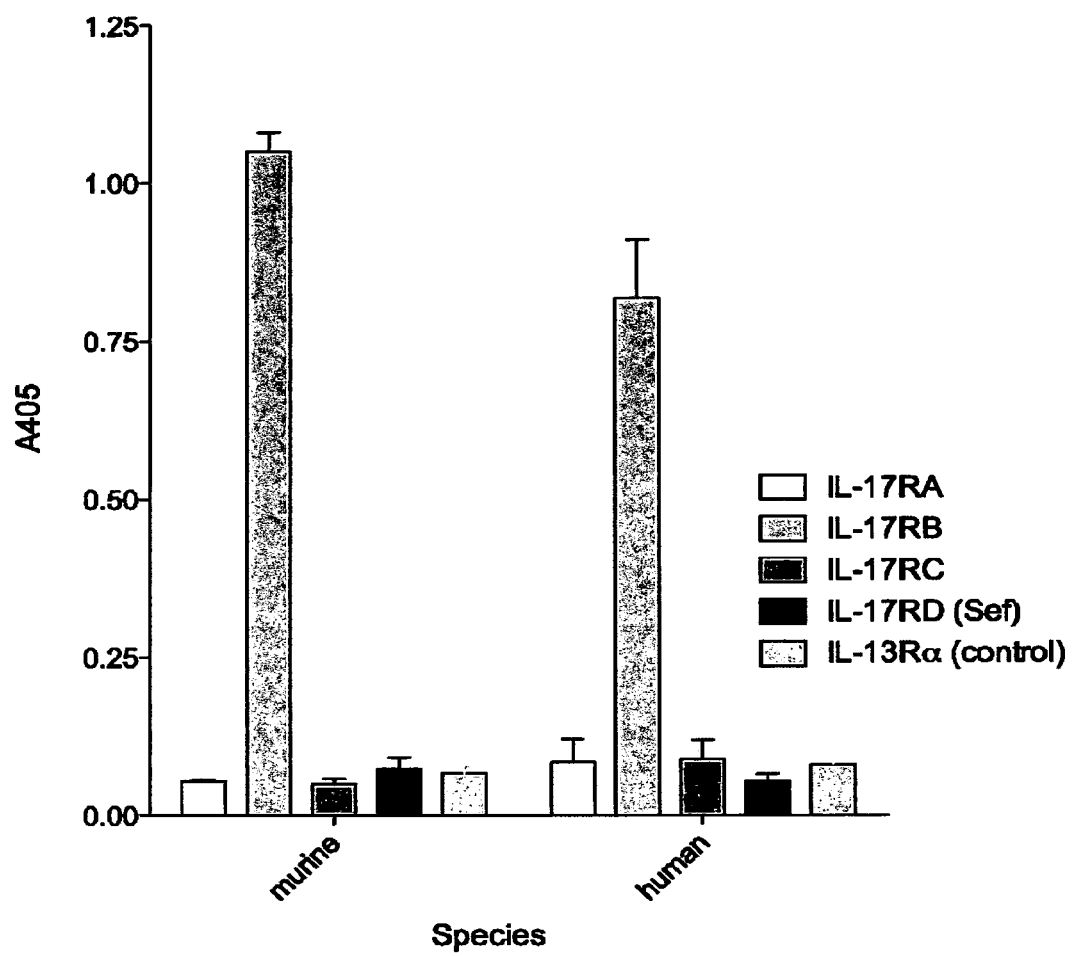
FIG. 3 shows that D9.2 binds IL-17BR but does not cross-react with mouse or human IL-17RA, IL-17RC, or IL-17RD. In brief, ELISA plates were coated with IL-17R-family members; IL-17RA, IL-17BR, IL-17RC or IL-17RD, or IL-13Rα control, at 2 µg/ml, incubated overnight at 4° C., washed in PBS/0.05% tween and blocked in PBS/10% FCS at room temperature for 4 hrs. Biotinylated D9.2 binding was detected using streptavidin-HRP and ELISA development solution and measuring absorbance at 405 nm.

The specificity of D9.2 was tested by assaying the interaction of D9.2 with other IL-17 receptor family members. D9.2 did not cross-react with IL-17A receptor (IL-17RA), IL-17C receptor (IL-17RC) or IL-17D receptor (IL-17RD)(FIG. 3).

Figure 4:
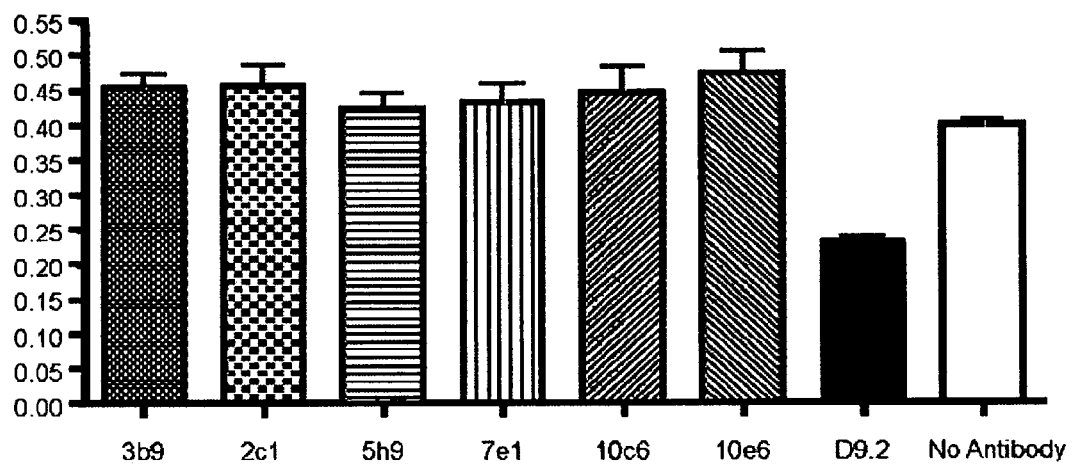
FIG. 4 shows that mouse monoclonal antibody D9.2, but not other mouse monoclonal anti-IL17BR antibodies (3b9, 2c1, 5h9, 7e1, 10c6, 10e6), inhibits the binding of human IL-25 to the human IL-25 receptor. Each purified mouse monoclonal antibody was diluted (×100) in hIL17Br/Fc (100 ng/ml) to a final concentration of 1 µg/ml in a hIL17Br/Fc solution at 100 ng/ml. In brief, [antibody×hIL17Br/Fc] mix was added to human IL-25-coated plates, incubated 1 hour 30 mins and washed three times. Anti-hIgG (Fc)-HRP conjugate (Serotec) was added to the plate and incubated for 45 mins at RT, washed three times and developed with TMB. Reaction was stopped with 1 M HCL. Optical density was read at 450 nm, and the reagent blank reading subtracted from all readings.

The screen identified several antibodies which bound IL-17RB, however only D9.2 was able to inhibit the interaction between human IL-25 and human IL-17BR (FIG. 4).

D9.2 was tested for its ability to inhibit the biological activity of IL-25. IL-25 induces the release of type-2 cytokines, such as IL-13, initially from innate non-B/non-T (NBNT) cells (Fallon et al., 2006; Fort et al., 2001) and from T cells (Angkasekwinai et al., 2007). Furthermore, both human TK-10 (a renal carcinoma cell line) and mouse renal carcinoma (RENCA) cell lines secrete the chemokine IL-8 (known as KC in the mouse) in response to stimulation with TNF-α and IL-25 (Sayers et al., 1990).

Figure 5:
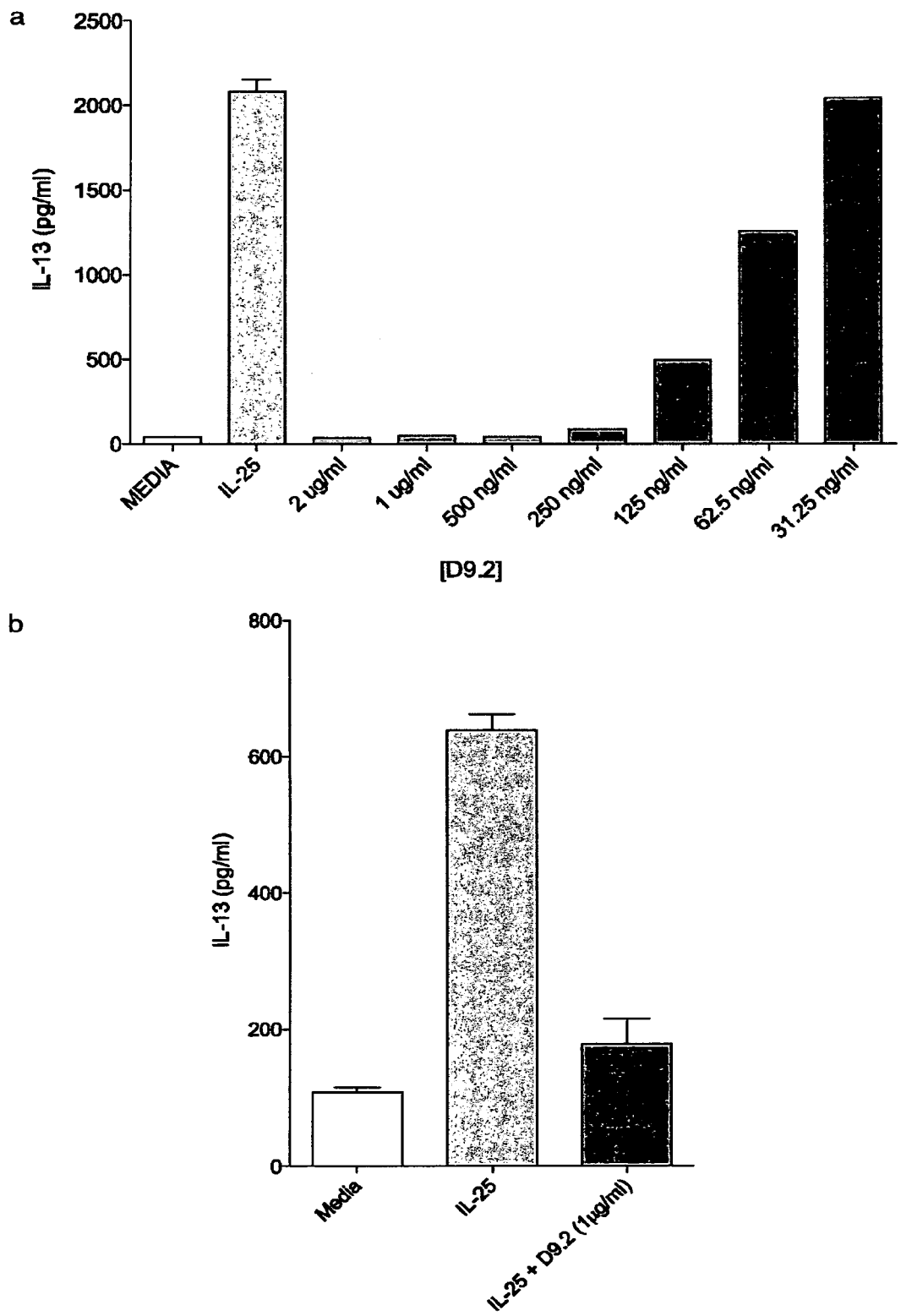
FIG. 5 shows that D9.2 antibodies block NBNT cell and CD4+ (T and/or NKT) cell IL-13 production in vitro. (a) NBNT cell. In brief, mysenteric lymph nodes were excised from naïve BALB/c mice and depleted of CD3+ and CD19+ cells. NBNT cells were plated on round bottomed 96-well plates at $3 \times 10^5$ cells/well and incubated for 72 hrs in RPMI 10% alone (MEDIA) or RPMI 10% FCS with 10 ng/ml IL-25 (IL-25). D9.2 was added to wells in serial dilution from a top concentration of 2 µg/ml and incubated for 1.5 hrs before addition of 10 ng/ml IL-25 to the wells. Plates were then incubated at 37° C. for 72 hrs before supernatants were tested for IL-13 content by ELISA. (b) CD4+ (T and/or NKT) cell. Spleens were taken from naïve wild-type BALB/c mice and a single cell suspension prepared. Isolated CD4+ cells were cultured at $1 \times 10^6$ cells/ml in 96-well plates either in RPMI alone or in RPMI supplemented with 10 ng/ml IL-25 with or without D9.2 at 1 µg/ml. Cells were cultured for 72 hrs before supernatants were taken for analysis of IL-13 protein levels by ELISA.

In an in vitro bioassay, D9.2 inhibited the bioactivity triggered by IL-17BR/IL-25 binding—i.e. IL-25-dependent production of IL-13 by primary mouse NBNT cells (FIG. 5a) and CD4+ T/NKT cells (FIG. 5b).

Figure 6:
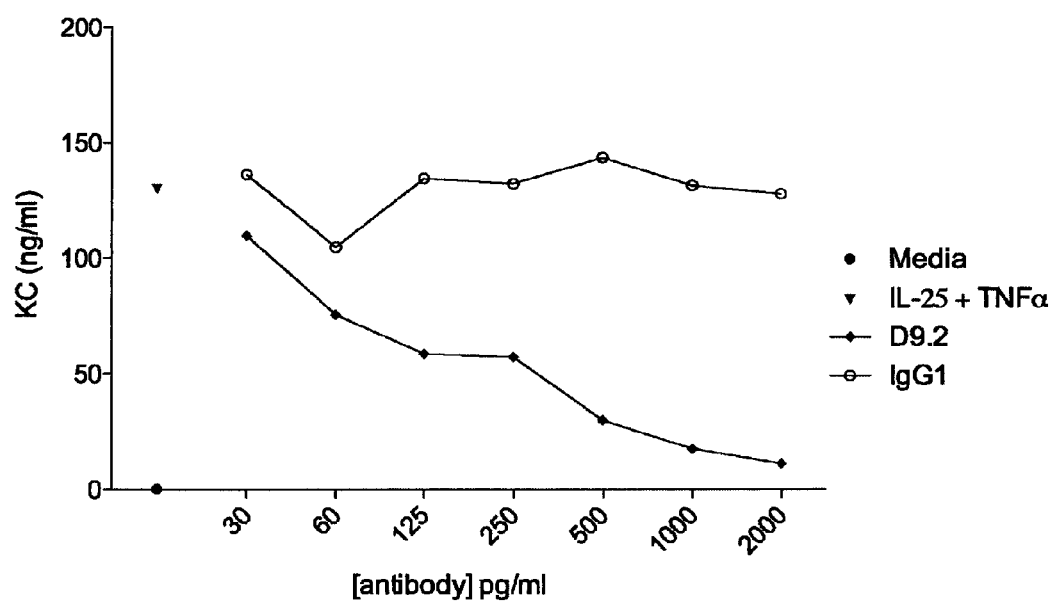
FIG. 6 shows that D9.2 inhibits IL-25-induced production of KC (mouse IL-8) from a mouse renal carcinoma (RENCA) cell line in a dose-dependent manner. IL-25 (100 ng/ml) was pre-incubated with varying concentrations of D9.2 or IgG1 control antibody for 30-60 minutes at room temperature prior to addition to cells. TNF-α (10 ng/ml) was added to RENCA cell-coated plates immediately prior to addition of the IL-25 protein/D9.2 mix. Control samples without antibody were incubated with 100 ng/ml of IL-25 and 10 ng/ml TNF-α (IL-25+TNF-α), or medium only control (Media), for 24 hrs before adding to the cells. Determination of KC release by ELISA was performed at 24 hrs post stimulation.

Furthermore, D9.2 inhibited KC production from IL-25-stimulated mouse RENCA cells in vitro (FIG. 6).

Figure 7:
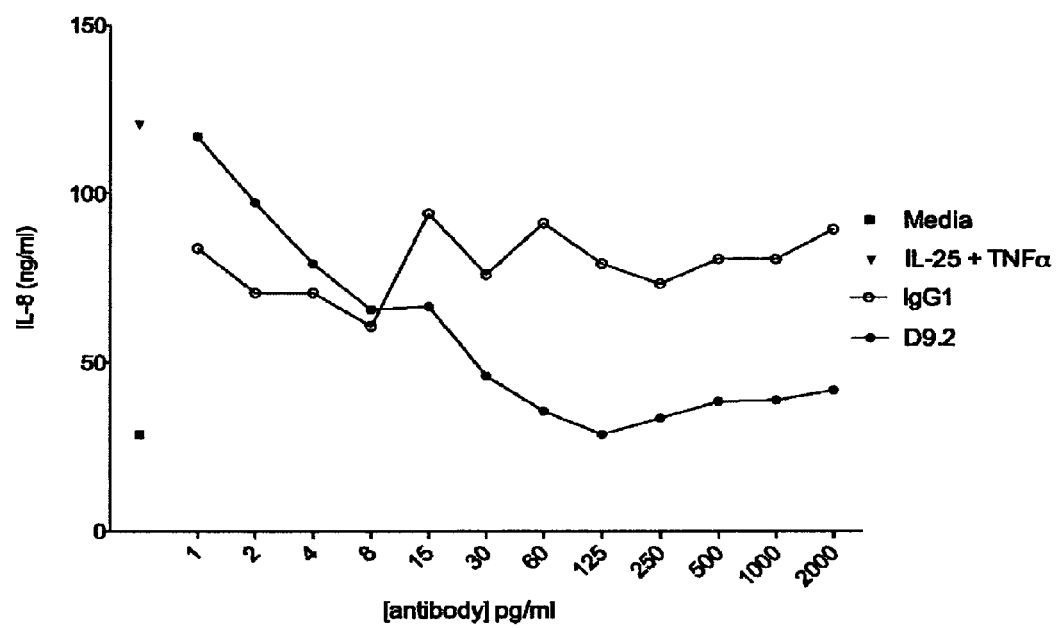
FIG. 7 shows that D9.2 inhibits IL-25-induced production of IL-8 from a human renal carcinoma (TK-10) cell line in a dose-dependent manner. IL-25 (100 ng/ml) was pre-incubated with varying concentrations of D9.2 or IgG1 control antibody for 30-60 minutes at room temperature. TNF-α (10 ng/ml) was added to TK-10 cell-coated plates immediately prior to addition of the IL-25 protein/D9.2 mix. Control samples without antibody were incubated with 100 ng/ml of IL-25 and 10 ng/ml TNF-α (IL-25+TNF-α), or medium only control (Media), for 24 hrs before adding to the cells. Determination of IL-8 release by ELISA was performed at 24 hrs post stimulation.

Significantly D9.2 was also able to inhibit the biological activity of human IL-25. D9.2 inhibited IL-25-dependent IL-8 secretion by human TK-10 cells in a dose-dependent fashion (FIG. 7).

The combination of these properties was investigated further in in vivo systems to demonstrate usefulness in the treatment of asthma. Additional experiments demonstrate efficacy in the treatment of IBD.

Example 3

Experimental Model of Allergic Asthma

BALB/c mice were first sensitized with the antigen OVA, before being challenged with aerosolised OVA. Sensitised and challenged BALB/c mice develop a distinctive asthma phenotype. This is characterised by increased AHR following exposure to the provocative agent methacholine, eosinophil infiltration of the airways, goblet cell hyperplasia and serum IgE secretion, as compared to control BALB/c mice challenged with PBS.

Using this model, BALB/c mice were treated at the challenge phase with either isotype control anti-c-myc IgG1 (clone 9E10.2) or anti-IL-17BR clone D9.2. Significantly, administration of D9.2 reduced the levels of IL-13 produced following antigen challenge and IL-5 produced following antigen restimulation to levels similar to those found in the absence of antigen challenge or in IL-17BR-deficient mice (FIGS. 8a and b). Numbers of IL-13-producing cells in the lungs of antigen challenged mice were also reduced to such levels (FIG. 8c). Similarly, disease-related expansion of gamma/delta T cells was also found to be blocked following treatment with D9.2 (FIG. 8d). Jin et al. (2007, J. Immunol.) have shown that the absence of gamma/delta T cells leads to an inability to develop AHR, suggesting that anti-IL-17BR antibody is able to inhibit two pathways known to be essential in the development of asthma—IL-13 production and gamma/delta T cell responsiveness. Furthermore, treatment with D9.2 reduced airways hyperreactivity, a key feature of human asthma, in a mouse model of asthma.

Example 4

Experimental Model of Inflammatory Bowel Disease (IBD)

BALB/c mice were first sensitized with the hapten oxazolone (OXA), before being challenged by intra-rectal injection of the same chemical. Sensitized and challenged mice develop a distinctive IBD phenotype, characterised by weight loss, shortening of the colon and inflammation in the large intestine, accompanied by blood in the stools (as compared to ethanol only controls).

Using this model, BALB/c mice were treated prior to both sensitization and challenge with OXA with either isotype control anti-KLH IgG1 or anti-IL17BR (clone D9.2). Administration of D9.2 reduced the disease index of the animals, resulting in a lower mortality rate (FIG. 9(a)) and improved clinical score, i.e. reduced clinical signs of IBD manifested in weight loss and the behaviour and appearance of the animals (FIG. 9(b)). Furthermore, D9.2 protected against the colon shortening that results from inflammation and haemorrhage (FIG. 9(c)), and the colons of mice treated with D9.2 showed less inflammation and haemorrhage in comparison with mice receiving anti-KLH control antibody.

Example 5

Cloning and Sequencing D9.2

To clone the immunoglobulin sequence from D9.2, RNA was isolated from the D9.2 cell clone and cDNA prepared by a reverse transcription reaction.

The immunoglobulin heavy chain (IgH) cDNA was amplified by PCR using a conserved 5' VH region primer, MHV2 (SEQ ID NO:11) in combination an IgG1 constant region primer MHCG1 (SEQ ID NO:12).

Similarly, immunoglobulin light chain (IgK) was amplified using a conserved 5' IgK region primers MKV3 (SEQ ID NO:13) in combination with the kappa constant region primer MKC (SEQ ID NO:14).

The thermostable polymerase Phusion (NEB F-531L) was used throughout for PCR reactions.

The D9.2 amplification products of VH2+MHCG1 were directly ligated into the pCRII® Blunt-TOPO® vector using the TOPO-blunt Cloning® kit (Cat 45-0245), as were the amplification products of the light chain amplification reaction. *E. coli* TOP10 bacteria transformed with the ligated pCRII-blunt vector constructs were cloned on LB-ampicillin-XGal agar plates, by picking white colonies onto an agar grid and into the PCR screening mixture. The cloned plasmid inserts were PCR-amplified. The amplification products were gel electrophoresed and the predicted products identified. Overnight cultures (5 ml) of each clone, producing the correct-sized PCR amplification product, were processed using the QIAprep Spin Miniprep Kit Protocol (cat 27106), to produce DNA plasmid minipreps. Each selected plasmid was sequenced in both directions using M13 forward and reverse primers.

The complete cycle of RT-PCR, cloning, and DNA sequence analysis was repeated to obtain two completely independent sets of sequence information for each immunoglobulin chain.

The complete deduced nucleotide sequence of the VH and Vkappa genes are shown as SEQ ID NO:1 and SEQ ID NO:3 respectively. These sequences include the leader sequences at the beginning of each variable gene segment which encodes a signal sequence which is used to transport the newly synthesized antibody chains into the endoplasmic reticulum; they are not present in the final heavy and light chains.

Immunology and Molecular Biology Reagents

| Article | UK Supplier | Catalog Number | Lot Numbers |
|---|---|---|---|
| 10β competent E. coli cells | NEB | C3019H | |
| Agarose (UltraPure ™) | Invitrogen | 15510-027 | 3048948 |
| Albumin bovine (BSA) | Sigma | A7030 | 086K1230 |
| Ampicillin | Sigma | A-9518 | 63H0992 |
| IL-25 (murine) | R&D Systems | | |
| IL-25 (human) | R&D Systems | | |
| Oligonucleotides | Sigma | n.a. | |
| Oxazolone | Sigma | E0753 | |
| PBS Tablets | Sigma | P4417 | 017K8212 |
| QIAprep Spin Miniprep Kit | Qiagen | 27106 | 127150290 |
| Quantikine Murine IL-13 ELISA Kit | R&D Systems | M1300CB | |
| Quick Ligation Kit | NEB | M2200s | |
| QuikChange ® II XL Site-Directed Mutagenesis Kit | Stratagene | 200522-5 | 0870486 |
| streptavidin-labelled dynabeads | Invitrogen | | |
| SYBR Safe DNA gel stain | Invitrogen | 33102 | 55081A |
| TOPO-blunt cloning ® kit | Invitrogen | 45-0245 | 1311906 |
| X-Gal | Promega | V394A | 20965701 |
| rhIL-17RD (Sef) | R&D systems | 2275-IL | NBR015031 |
| rmIL-17RD (Sef) | R&D systems | 2276-ML | NAF014111 |
| rhIL-17RC | R&D systems | 2269-IL | NCJ0208081 |
| rmIL-17RC | R&D systems | 2270-ML | |
| rhIL-17BR-Fc | R&D systems | 1207-BR | |
| rmIL-17BR-Fc | R&D systems | 1040-BR | |
| rhIL-17RA-Fc | R&D systems | 177-IR | |
| rmIL-17RA-Fc | R&D systems | 4481-MR | |
| Mouse CXCL1/KC Quantikine ELISA Kit | R&D systems | MKC00B | |
| Human CXCL8/IL-8 Quantikine ELISA Kit | R&D systems | D8000C | |

ABBREVIATIONS

AHR Airways hyperreactivity
° C. Centigrade
bp Base pairs
CD Crohn's disease
CDR Complementarity determining region
DMEM Dulbecco's Modified Eagles Medium
DNA Deoxyribonucleic acid
ELISA Enzyme linked immuno-adsorbent assay
FACS Fluorescence activated cell sorting
FCS Foetal calf serum
g Grams
hr Hour
HRP Horseradish peroxidase
IBD Inflammatory bowel disease
Ig Immunoglobulin
i.p. intraperitoneal
KLH Keyhole Limpet Hemocyanin
mAb Monoclonal antibody
min Minute
NBNT Non B/Non T cells isolated from mouse mesenteric lymph nodes
nm Nanometer
OD Optical density
OVA Ovalbumin
OXA Oxazolone
PBS Phosphate buffered saline
PCR Polymerase chain reaction
RENCA renal carcinoma
RH Recombinant heavy chain
RK Recombinant kappa chain
TMB 3,3',5,5' tetramethylbenzidine
UC Ulcerative colitis
VH Immunoglobulin heavy chain variable region
VL Immunoglobulin light chain variable region
VK Immunoglobulin kappa light chain variable region

Sequences

SEQ ID NO: 1 D9.2 VH encoding nucleotide sequence
cttcttcttagcaacacctacatgtgtccactcccaggtccaattgcagcagcctggggctgagctggt
gaggcctggggcttcagtgaagctgtcctgcaagacttctggctacacgttcatcagttattggatgaa
ctgggttaagcaggggcctgagcaaggccttgagtggattggaagaattgatccttacgatagtgaaat
tcagtacaatcaaaagttcaaggacaaggccatattgactgtagacaaatcctccagcgcagcctacat
gcaactcatcagcctgacatctgaggactctgcggtctattactgtgcaagatcgggggtttcgactg
gtttgcgtactggggccaagggactctggtcactgtctctgcagccaaaacgacacccccatcagtcta
tccactgaagggcgaattccagcacactggcggccgttac SEQ ID NO: 2 D9.2 VH amino acid sequence
FFLATPTCVHSQVQLQQPGAELVRPGASVKLSCKTSGYTFISYWMNWVKQGGPEQGLEWIGRIDPYDSE
IQYNQKFKDKAILTVDKSSSAAYMQLISLTSEDSAVYYCARSGGFDWFAYWGQGTLVTVS SEQ ID NO: 3 D9.2 VL encoding nucleotide sequence
atgagtgtgctcactcaggtcctggcgttgctgctgctgtggcttacagatgccagatgtgacatccag
atgactcagtctccagcctccctatctgtatctgtgggagaaactgtcaccatcacatgtcgagcaagt
gagaatattaacagtaatttagcatggtatcagcagaaaaagggaaaatctcctcagctcctggtctat
gatgtaacaaacttagcagatggtgtgccatcaaggttcagtggcagtggatcaggcacacaatattcc
ctcaagatcaacagcctgcagtctgaagattttgggagttattactgtcaacattttggcgtcctccg
tacacgttcggaggggggaccaatctggaaataaaa SEQ ID NO: 4 D9.2 VL amino acid sequence
MSVLTQVLALLLLWLTDARCDIQMTQSPASLSVSVGETVTITCRASENINSNLAWYQQKKGKSPQLLVY
DVTNLADGVPSRFSGSGSGTQYSLKINSLQSEDFGSYYCQHFWRPPYTFGGGTNLEIK SEQ ID NO: 5 D9.2 VH CDR1 amino acid sequence
SYWMN SEQ ID NO: 6 D9.2 VH CDR2 amino acid sequence
RIDPYDSEIQYNQKFKD SEQ ID NO: 7 D9.2 VH CDR3 amino acid sequence
SGGFDWFAY SEQ ID NO: 8 D9.2 VL CDR1 amino acid sequence
RASENINSNLA SEQ ID NO: 9 D9.2 VL CDR2 amino acid sequence
DVTNLAD SEQ ID NO: 10 D9.2 VL CDR3 amino acid sequence
QHFWRPPYT SEQ ID NO: 11 MHV2 primer sequence
atgggatggagctrtatcatsytctt (r = a/g, s = c/g, y = t/c)

SEQ ID NO: 12 MHCG1 primer sequence
cagtggatagacagatgggggg

SEQ ID NO: 13 MKV3 primer sequence
atgagtgtgctcactcaggtcctggsgttg

SEQ ID NO: 14 MKC primer sequence
actggatggtgggaagatgg

REFERENCES

1. Angkasekwinai, P., et al., *J Exp Med* 204, 1509-1517 (2007)
2. Ballantyne, S. J., et al., *J Allergy Clin Immunol* (2007)
3. Fallon, P. G., et al., *J Exp Med* 203, 1105-1116 (2006).
4. Fort, M. M., et al., *Immunity* 15, 985-995 (2001).
5. Lajoie-Kadoch, S., *Am J Physiol Lung Cell Mol Physiol* 290, L1238-46.
6. Lee, J., et al., *J Biol Chem* 276, 1660-1664 (2001).
7. Moseley, T. A., et al., *Cytokine Growth Factor Rev* 14, 155-174 (2003).
8. Owyang, A. M., et al., (2006) *J Exp Med* 203, 843-849.
9. Pan, G., et al., *J Immunol* 167, 6559-6567 (2001).
10. Shi, Y., et al., *J Biol Chem* 275, 19167-19176 (2000).
11. Tian, E., et al., *Oncogene* 19, 2098-2109 (2000).
12. Wang, Y. H., et al., *J Exp Med* 204, 1837-1847 (2007).
13. Rickel E. A., et al., *J Immunol* 181, 4299-4310 (2008).
14. Sayers T. J., et al., *Cancer Res* 50, 5414-5420 (1990).
15. Jin N., et al., *J Immunol* 179, 2961-2968 (2007).
16. Heller, F., et al., *Immunity* 17:629-638 (2002).
17. Fichtner-Feigl, S., et al., *Mucosal Immunology* 1 Suppl 1:S24-27 (2008).
18. Buning, C., et al. *Eur J Immunogenet* 30:329-333 (2003).
19. Hanauer, S. B., *Alimentary pharmacology & therapeutics* 27 Suppl 1:15-21 (2008).
20. Wang, X., et al., *Chinese Journal of Digestive Diseases* 5, 165-168 (2004)

The invention claimed is:

1. A method for the treatment or reduction of inflammatory bowel disease, said method comprising administering to a subject in need thereof an effective amount of an antibody molecule which binds IL-17BR and which comprises
   an antibody VH domain comprising a CDR1 having an amino acid sequence as set out in SEQ ID NO:5, a CDR2 having an amino acid sequence as set out in SEQ ID NO:6, and a CDR3 having an amino acid sequence as set out in SEQ ID NO:7, and
   an antibody VL domain with a CDR1 having an amino acid sequence as set out in SEQ ID NO:8, a CDR2 having an amino acid sequence as set out in SEQ ID NO:9, and a CDR3 having an amino acid sequence as set out in SEQ ID NO:10,
   optionally in a pharmaceutically acceptable carrier.

2. The method of claim 1, wherein the inflammatory bowel disease is ulcerative colitis or Crohn's disease.

3. The method of claim 1, wherein the VH domain comprises a human framework region.

4. The method of claim 1, wherein the VH domain comprises SEQ ID NO:2.

5. The method of claim 1, wherein the VL domain comprises a human framework region.

6. The method of claim 1, wherein the VL domain comprises SEQ ID NO: 4.

7. The method of claim 1, wherein the antibody molecule is a Fab, F(ab')$_2$, or single chain variable fragment (scFv) antibody fragment.

8. The method of claim 1, wherein the antibody molecule comprises an antibody constant region.

9. The method of claim 8, wherein the constant region is an IgG1 or IgG4 constant region.

10. The method of claim 8, wherein the antibody molecule comprises a whole antibody.

* * * * *

SEQUENCE LISTING

<160> NUMBER OF SEQ ID NOS: 14

<210> SEQ ID NO 1
<211> LENGTH: 454
<212> TYPE: DNA
<213> ORGANISM: Mus musculus

<400> SEQUENCE: 1
cttcttctta gcaacaccta catgtgtcca ctcccaggtc caattgcagc agcctggggc      60
tgagctggtg aggcctgggg cttcagtgaa gctgtcctgc aagacttctg gctacacgtt     120
catcagttat tggatgaact gggttaagca ggggcctgag caaggccttg agtggattgg     180
aagaattgat ccttacgata gtgaaattca gtacaatcaa aagttcaagg acaaggccat     240
attgactgta gacaaatcct ccagcgcagc ctacatgcaa ctcatcagcc tgacatctga     300
ggactctgcg gtctattact gtgcaagatc gggggtttc gactggtttg cgtactgggg       360
ccaagggact ctggtcactg tctctgcagc caaaacgaca ccccccatcag tctatccact     420 gaagggcgaa ttccagcaca ctggcggccg ttac                                  454

<210> SEQ ID NO 2
<211> LENGTH: 129
<212> TYPE: PRT
<213> ORGANISM: Mus musculus

<400> SEQUENCE: 2

Phe Phe Leu Ala Thr Pro Thr Cys Val His Ser Gln Val Gln Leu Gln
1               5                   10                  15

Gln Pro Gly Ala Glu Leu Val Arg Pro Gly Ala Ser Val Lys Leu Ser
            20                  25                  30

Cys Lys Thr Ser Gly Tyr Thr Phe Ile Ser Tyr Trp Met Asn Trp Val
        35                  40                  45

Lys Gln Gly Gly Pro Glu Gln Gly Leu Glu Trp Ile Gly Arg Ile Asp
    50                  55                  60

Pro Tyr Asp Ser Glu Ile Gln Tyr Asn Gln Lys Phe Lys Asp Lys Ala
65                  70                  75                  80

Ile Leu Thr Val Asp Lys Ser Ser Ala Ala Tyr Met Gln Leu Ile
                85                  90                  95

Ser Leu Thr Ser Glu Asp Ser Ala Val Tyr Tyr Cys Ala Arg Ser Gly
            100                 105                 110

Gly Phe Asp Trp Phe Ala Tyr Trp Gly Gln Gly Thr Leu Val Thr Val
        115                 120                 125

Ser

<210> SEQ ID NO 3
<211> LENGTH: 381
<212> TYPE: DNA
<213> ORGANISM: Mus musculus

<400> SEQUENCE: 3
atgagtgtgc tcactcaggt cctggcgttg ctgctgctgt ggcttacaga tgccagatgt      60
gacatccaga tgactcagtc tccagcctcc ctatctgtat ctgtgggaga aactgtcacc     120
atcacatgtc gagcaagtga gaatattaac agtaatttag catggtatca gcagaaaaag     180
ggaaaatctc ctcagctcct ggtctatgat gtaacaaact agcagatgg tgtgccatca       240 aggttcagtg gcagtggatc aggcacacaa tattccctca agatcaacag cctgcagtct     300

```
gaagattttg ggagttatta ctgtcaacat ttttggcgtc ctccgtacac gttcggaggg    360
gggaccaatc tggaaataaa a                                              381
```

<210> SEQ ID NO 4
<211> LENGTH: 127
<212> TYPE: PRT
<213> ORGANISM: Mus musculus

<400> SEQUENCE: 4

```
Met Ser Val Leu Thr Gln Val Leu Ala Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Asn Ser Asn Leu Ala Trp Tyr Gln Gln Lys Gly Lys Ser Pro
    50                  55                  60

Gln Leu Leu Val Tyr Asp Val Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Phe Gly Ser Tyr Tyr Cys Gln His Phe Trp
            100                 105                 110

Arg Pro Pro Tyr Thr Phe Gly Gly Gly Thr Asn Leu Glu Ile Lys
        115                 120                 125
```

<210> SEQ ID NO 5
<211> LENGTH: 5
<212> TYPE: PRT
<213> ORGANISM: Mus musculus

<400> SEQUENCE: 5

```
Ser Tyr Trp Met Asn
1               5
```

<210> SEQ ID NO 6
<211> LENGTH: 17
<212> TYPE: PRT
<213> ORGANISM: Mus musculus

<400> SEQUENCE: 6

```
Arg Ile Asp Pro Tyr Asp Ser Glu Ile Gln Tyr Asn Gln Lys Phe Lys
1               5                   10                  15

Asp
```

<210> SEQ ID NO 7
<211> LENGTH: 9
<212> TYPE: PRT
<213> ORGANISM: Mus musculus

<400> SEQUENCE: 7

```
Ser Gly Gly Phe Asp Trp Phe Ala Tyr
1               5
```

<210> SEQ ID NO 8
<211> LENGTH: 11
<212> TYPE: PRT
<213> ORGANISM: Mus musculus

-continued

<400> SEQUENCE: 8

Arg Ala Ser Glu Asn Ile Asn Ser Asn Leu Ala
1 5 10

<210> SEQ ID NO 9
<211> LENGTH: 7
<212> TYPE: PRT
<213> ORGANISM: Mus musculus

<400> SEQUENCE: 9

Asp Val Thr Asn Leu Ala Asp
1 5

<210> SEQ ID NO 10
<211> LENGTH: 9
<212> TYPE: PRT
<213> ORGANISM: Mus musculus

<400> SEQUENCE: 10

Gln His Phe Trp Arg Pro Pro Tyr Thr
1 5

<210> SEQ ID NO 11
<211> LENGTH: 26
<212> TYPE: DNA
<213> ORGANISM: Artificial
<220> FEATURE:
<223> OTHER INFORMATION: Synthetic sequence: MHV2 primer

<400> SEQUENCE: 11
atgggatgga gctrtatcat sytctt 26

<210> SEQ ID NO 12
<211> LENGTH: 21
<212> TYPE: DNA
<213> ORGANISM: Artificial
<220> FEATURE:
<223> OTHER INFORMATION: Synthetic sequence: MHCG1 primer

<400> SEQUENCE: 12
cagtggatag acagatgggg g 21

<210> SEQ ID NO 13
<211> LENGTH: 30
<212> TYPE: DNA
<213> ORGANISM: Artificial
<220> FEATURE:
<223> OTHER INFORMATION: Synthetic sequence: MKV3 primer

<400> SEQUENCE: 13
atgagtgtgc tcactcaggt cctggsgttg 30

<210> SEQ ID NO 14
<211> LENGTH: 20
<212> TYPE: DNA
<213> ORGANISM: Artificial
<220> FEATURE:
<223> OTHER INFORMATION: Synthetic sequence: MKC primer

<400> SEQUENCE: 14
actggatggt gggaagatgg 20